(12) United States Patent
Kassab et al.

(10) Patent No.: US 10,952,678 B2
(45) Date of Patent: Mar. 23, 2021

(54) DEVICES AND SYSTEMS FOR TISSUE ENGAGEMENT AND METHODS OF USING THE SAME

(71) Applicants: Ghassan S. Kassab, La Jolla, CA (US); Zachary Berwick, San Diego, CA (US); Matthew Phillips, Carlsbad, CA (US)

(72) Inventors: Ghassan S. Kassab, La Jolla, CA (US); Zachary Berwick, San Diego, CA (US); Matthew Phillips, Carlsbad, CA (US)

(73) Assignee: CVDevices, LLC, San Diego, CA (US)

( * ) Notice: Subject to any disclaimer, the term of this patent is extended or adjusted under 35 U.S.C. 154(b) by 569 days.

(21) Appl. No.: 15/499,240

(22) Filed: Apr. 27, 2017

(65) Prior Publication Data
US 2017/0224283 A1     Aug. 10, 2017

Related U.S. Application Data

(63) Continuation-in-part of application No. PCT/US2017/017178, filed on Feb. 9, 2017.

(60) Provisional application No. 62/380,344, filed on Aug. 26, 2016, provisional application No. 62/328,357, filed on Apr. 27, 2016, provisional application No.
(Continued)

(51) Int. Cl.
| | |
|---|---|
| *A61B 5/00* | (2006.01) |
| *A61B 17/34* | (2006.01) |
| *A61B 17/00* | (2006.01) |
| *A61B 5/0538* | (2021.01) |

(Continued)

(52) U.S. Cl.
CPC .......... *A61B 5/6885* (2013.01); *A61B 5/0084* (2013.01); *A61B 5/0538* (2013.01); *A61B 17/3478* (2013.01); *A61B 2017/00026* (2013.01); *A61B 2017/308* (2013.01); *A61B 2090/3966* (2016.02); *A61B 2562/0247* (2013.01)

(58) Field of Classification Search
CPC .......... A61B 5/0538; A61B 2090/3966; A61B 2017/308; A61B 5/6846–6886
See application file for complete search history.

(56) References Cited

U.S. PATENT DOCUMENTS

| | | | |
|---|---|---|---|
| 2002/0077627 A1* | 6/2002 | Johnson | A61B 18/1477 606/41 |
| 2005/0113760 A1* | 5/2005 | Chachques | A61N 1/0573 604/174 |

(Continued)

*Primary Examiner* — Keith M Raymond
*Assistant Examiner* — Milton Truong
(74) *Attorney, Agent, or Firm* — Mark C. Reichel; Natalie J. Dean; Reichel Stohry Dean LLP

(57) ABSTRACT

Devices and systems for tissue engagement and methods of using the same. In at least one embodiment of a device of the present disclosure, the device comprises an elongated body having a proximal end, a distal end, and at least one lumen extending from the proximal end to the distal end; an engagement portion at the distal end of the elongated body, the engagement portion configured to engage a tissue adjacent thereto when the engagement portion contacts the tissue while suction is applied through the device; and at least one electrode present along the engagement portion and configured to contact the tissue when the engagement portion contacts the tissue and to obtain bioimpedance data from the tissue while suction is applied through the device.

13 Claims, 19 Drawing Sheets

Related U.S. Application Data

62/293,193, filed on Feb. 9, 2016, provisional application No. 62/328,343, filed on Apr. 27, 2016.

(51) Int. Cl.
*A61B 17/30* (2006.01)
*A61B 90/00* (2016.01)

(56) References Cited

U.S. PATENT DOCUMENTS

| | | | | |
|---|---|---|---|---|
| 2006/0241583 A1* | 10/2006 | Malecki | ............ | A61B 17/0057 606/41 |
| 2007/0088203 A1* | 4/2007 | Lau | ................... | A61B 17/0218 600/205 |
| 2013/0190813 A1* | 7/2013 | Tegels | ............... | A61B 17/0057 606/214 |
| 2014/0235957 A1* | 8/2014 | Addington | .......... | A61J 15/0046 600/301 |
| 2015/0112257 A1* | 4/2015 | Byrne | ................... | A61M 25/10 604/103.02 |
| 2016/0058458 A1* | 3/2016 | Hansen | ............... | A61B 17/221 606/200 |
| 2016/0089172 A1* | 3/2016 | Windheuser | ....... | A61B 1/00085 606/115 |
| 2017/0106185 A1* | 4/2017 | Orts | ................... | A61N 1/0573 |

* cited by examiner

DEVICES AND SYSTEMS FOR TISSUE ENGAGEMENT AND METHODS OF USING THE SAME

PRIORITY

The present application a) is related to, claims the priority benefit of, and is a bypass continuation-in-part patent application consistent with and according to 35 U.S.C. 120 and 35 U.S.C. 363 of, International Patent Application Serial No. PCT/US2017/017178, filed Feb. 9, 2017, which is related to, and claims the priority benefit of, U.S. Patent Application Ser. No. 62/380,344, filed Aug. 26, 2016, U.S. Patent Application Ser. No. 62/328,357, filed Apr. 27, 2016, and U.S. Patent Application Ser. No. 62/293,193, filed Feb. 9, 2016, b) is related to, and claims the priority benefit of, U.S. Patent Application Ser. No. 62/328,343, filed Apr. 27, 2016, c) is related to, and claims the priority benefit of, U.S. Patent Application Ser. No. 62/328,357, filed Apr. 27, 2016, and d) is related to, and claims the priority benefit of, U.S. Patent Application Ser. No. 62/380,344, filed Aug. 26, 2016. The entire contents of these applications are also incorporated herein in their entirety and by reference. The contents of U.S. Pat. No. 7,454,244 to Kassab et al., and U.S. U.S. Pat. No. 8,328,752 of Kassab et al., and U.S. Pat. No. 8,894,606 to Kassab et al. are also expressly incorporated herein by reference.

BACKGROUND

Suctional engagement of tissues using a device, such as during an interventional procedure, is complex and requires small devices to accomplish the same. However, several devices currently used by medical practitioners either do not provide enough suctional engagement to perform a necessary procedure, or are too large to perform such a procedure. Effective devices and systems for use with suction to effectively engage tissues would be well received in the marketplace.

During various medical procedures, injection of a substance into a tissue of interest occurs, and it is oftentimes critical that the substance be injected only into said tissue and not otherwise into the body, such as within the bloodstream, as said migrated substance could form an embolus and cause a clot, for example. When such a procedure is performed using a suction engagement catheter, for example, knowledge of actual suction engagement is important.

In view of the same, devices and systems configured to identify and ensure suction engagement to a tissue of interest, and methods of using the same, would be well received in the marketplace.

BRIEF SUMMARY

In an exemplary embodiment of a device of the present disclosure, the device comprises one or more of the following: an inner tube, an outer tube, and a foldable portion, whereby movement of the two tubes relative to one another causes the foldable portion to form a suction cup, and conversely causes a suction cup to form a foldable portion, depending on the direction of relative movement. Said devices, in various embodiments, are configured to deliver a liquid material, such as alginate, to a tissue of interest, such as cardiac tissue, to treat heart failure.

In at least one embodiment of a device of the present disclosure, the device comprises an outer tube positioned around an inner tube having at least one inner lumen defined therethrough, whereby the outer tube and the inner tube are connected together at a distal end of the device; and a foldable portion coupled to the outer tube; wherein movement of the outer tube relative to the inner tube in a first direction causes the foldable portion to fold, forming a suction cup at the distal end of the device. In at least one embodiment of a device of the present disclosure, the foldable portion comprises a plurality of flanges. In at least one embodiment of a device of the present disclosure, the plurality of flanges comprise a plurality of arcuate flanges. In at least one embodiment of a device of the present disclosure, a configuration of the plurality of flanges defines a configuration of the suction cup. In at least one embodiment of a device of the present disclosure, a distal tapered portion is present along the device between the foldable portion and the distal end of the device. In at least one embodiment of a device of the present disclosure, a proximal tapered portion is present along the device adjacent to the foldable portion. In at least one embodiment of a device of the present disclosure, the suction cup defines an interior environment having a larger cross-sectional area than a cross-section of the at least one inner lumen defined within the inner tube.

In at least one embodiment of a device of the present disclosure, movement of the outer tube relative to the inner tube in a second direction opposite the first direction causes the suction cup to fold so that the suction cup is no longer present. In at least one embodiment of a device of the present disclosure, the device forms part of a system, the system further comprising a sleeve positioned at least partially around the device, and/or a delivery catheter positioned at least partially within the at least one inner lumen of the device, and/or a needle positioned at least partially within the at least one inner lumen of the device, and/or a needle positioned at least partially within the delivery catheter, and/or a wire positioned at least partially within the needle. In at least one embodiment of a device of the present disclosure, the device is configured so that when foldable portion is folded to form the suction cup, suction through the at least one inner lumen of the device can cause the suction cup to suctionally engage a tissue or organ adjacent to the suction cup. In at least one embodiment of a device of the present disclosure, the at least one inner lumen comprises a single inner lumen, two inner lumens, three inner lumens, or four or more inner lumens.

In at least one embodiment of a device of the present disclosure, the device further comprises a first foldable bellows portion coupled to the outer tube proximal to the foldable portion, wherein movement of the outer tube relative to the inner tube in the first direction also causes the first foldable bellows portion to fold, forming a first bellows. In at least one embodiment of a device of the present disclosure, the first bellows portion comprises a plurality of flanges. In at least one embodiment of a device of the present disclosure, the plurality of flanges comprise a plurality of arcuate flanges. In at least one embodiment of a device of the present disclosure, the device further comprises a second foldable bellow portion coupled to the outer tube proximal to the first foldable portion, wherein movement of the outer tube relative to the inner tube in the first direction also causes the second foldable bellows portion to fold, forming a second bellows. In at least one embodiment of a device of the present disclosure, a distal tapered portion is present along the device between the foldable portion and the distal end of the device. In at least one embodiment of a device of the present disclosure, a proximal tapered portion is present along the device adjacent to the foldable portion. In at least one embodiment of a device of the present disclosure, the suction cup defines an interior environment having a larger cross-sectional area than a cross-section of the at least one inner lumen defined within the inner tube.

In at least one embodiment of a device of the present disclosure, movement of the outer tube relative to the inner tube in a second direction opposite the first direction causes the suction cup to fold so that the suction cup is no longer present. In at least one embodiment of a device of the present disclosure, movement of the outer tube relative to the inner tube in the second direction opposite the first direction causes the first foldable bellows portion fold so that the first bellows is no longer present. In at least one embodiment of a device of the present disclosure, the device forms part of a system, the system further comprising a sleeve positioned at least partially around the device, and/or a delivery catheter positioned at least partially within the at least one inner lumen of the device, and/or a needle positioned at least partially within the at least one inner lumen of the device, and/or a needle positioned at least partially within the delivery catheter, and/or a wire positioned at least partially within the needle. In at least one embodiment of a device of the present disclosure, the device is configured so that when foldable portion is folded to form the suction cup, suction through the at least one inner lumen of the device can cause the suction cup to suctionally engage a tissue or organ adjacent to the suction cup. In at least one embodiment of a device of the present disclosure, the at least one inner lumen comprises a single inner lumen, two inner lumens, three inner lumens, or four or more inner lumens. In at least one embodiment of a device of the present disclosure, the device comprises an outer tube defining at least one inner lumen therethrough; a compliant suction cup positioned at a distal end of the device; and a first bellows positioned between the outer tube and the compliant suction cup. In at least one embodiment of a device of the present disclosure, the device forms part of a system, the system further comprising a sleeve positioned at least partially around the device, and/or a delivery catheter positioned at least partially within the at least one inner lumen of the device, and/or a needle positioned at least partially within the at least one inner lumen of the device, and/or a needle positioned at least partially within the delivery catheter, and/or a wire positioned at least partially within the needle. In at least one embodiment of a device of the present disclosure, the device is configured so that suction through the at least one inner lumen of the device can cause the suction cup to suctionally engage a tissue or organ adjacent to the suction cup. In at least one embodiment of a device of the present disclosure, the device is configured so that suction through the at least one inner lumen of the device can cause the suction cup to collapse so that the first bellows collapses upon the suction cup. In at least one embodiment of a device of the present disclosure, the at least one inner lumen comprises a single inner lumen, two inner lumens, three inner lumens, or four or more inner lumens.

In at least one embodiment of a device of the present disclosure, the device comprises an outer tube defining at least one inner lumen therethrough, the outer tube having a notch or groove defined therein at or near a distal end of the outer tube; a balloon positioned at or near the distal end of the outer tube upon the notch or groove, the balloon configured for inflation via an inflation tube positioned relative to elongated body or defined within elongated body; wherein the balloon, upon inflation, is configured so that suction through the at least one inner lumen of the device can cause the inflated balloon to suctionally engage a tissue or organ adjacent to the inflated balloon. In at least one embodiment of a device of the present disclosure, the device further comprises a distal tube element positioned at the distal end of the outer tube distal to the balloon. In at least one embodiment of a device of the present disclosure, the inflated balloon has a donut shape, a funnel shape, or is configured as a bellows. In at least one embodiment of a device of the present disclosure, the balloon is inflatable by way of operating an inflation source coupled to the device. In at least one embodiment of a device of the present disclosure, the inflated balloon defines an interior environment having a larger cross-sectional area than a cross-section of the at least one inner lumen defined within the outer tube.

In at least one embodiment of a device of the present disclosure, the device forms part of a system, the system further comprising a sleeve positioned at least partially around the device, and/or a delivery catheter positioned at least partially within the at least one inner lumen of the device, and/or a needle positioned at least partially within the at least one inner lumen of the device, and/or a needle positioned at least partially within the delivery catheter, and/or a wire positioned at least partially within the needle. In at least one embodiment of a device of the present disclosure, the at least one inner lumen comprises a single inner lumen, two inner lumens, three inner lumens, or four or more inner lumens.

The present disclosure also includes disclosure of devices configured to suctionally engage a tissue, as described and/or shown herein. Said devices can be configured to provide feedback to a user to confirm sectional tissue engagement. Said devices can form forming part of a system, along with one or more of a vacuum source, an injection source, a console, and/or a needle. Said devices can comprise one or more electrodes configured to obtain impedance/conductance data (bioimpedance data) and/or comprise one or more radiopaque elements, whereby said radiopaque elements can also be configured to obtain impedance/conductance data (bioimpedance data). Various devices of the present disclosure can comprise one or more optical elements/sensors and/or one or more pressure elements/sensors. Various devices of the present disclosure can comprise a suction cup and optionally one or more bellows. Various devices of the present disclosure can comprise a vacuum gauge mechanism. Various devices of the present disclosure are configured to obtain impedance/conductance data (bioimpedance data), whereby the bioimpedance data can indicate whether or not various portions of the device contact a tissue or not. Various devices of the present disclosure can be configured so that the one or more electrodes and/or the one or more radiopaque elements, regardless of positioning on an elongated body of the device, a distal end of the device, upon a suction cup of the device, and/or upon the bellows of the device, are configured to obtain impedance/conductance data (bioimpedance data).

The present disclosure includes disclosure of a needle, as described and/or shown herein.

In at least one embodiment of a device of the present disclosure, the device comprises an elongated body having a proximal end, a distal end, and at least one lumen extending from the proximal end to the distal end; an engagement portion at the distal end of the elongated body, the engagement portion configured to engage a tissue adjacent thereto when the engagement portion contacts the tissue while suction is applied through the device; and at least one electrode present along the engagement portion and configured to contact the tissue when the engagement portion contacts the tissue and to obtain bioimpedance data from the tissue while suction is applied through the device.

In at least one embodiment of a device of the present disclosure, the engagement portion comprises a compliant suction cup, and wherein the at least one electrode is present along the suction cup.

In at least one embodiment of a device of the present disclosure, the engagement portion further comprises a bellows adjacent to the suction cup, the bellows configured to move relative to the suction cup when suction is applied through the device.

In at least one embodiment of a device of the present disclosure, the device further comprises a first radiopaque element present along the suction cup and configured to contact the tissue when the suction cup contacts the tissue.

In at least one embodiment of a device of the present disclosure, the device further comprises a second radiopaque element present along the bellows; wherein the first radiopaque element and the second radiopaque element do not contact one another when no suction is applied through the device; and wherein the first radiopaque element and the second radiopaque element contact one another when suction is applied through the device.

In at least one embodiment of a device of the present disclosure, when a needle is positioned within the device and wherein when the needle and the at least one electrode contact the tissue while suction is applied through the device, a circuit is created between the at least one electrode and the needle, whereby the circuit is indicative of suction contact of the electrode to the tissue and/or needle contact of the tissue.

In at least one embodiment of a device of the present disclosure, the device further comprises a first radiopaque element present along the engagement portion and configured to contact the tissue when the engagement portion contacts the tissue.

In at least one embodiment of a device of the present disclosure, the first radiopaque element is configured to obtain bioimpedance data from the tissue when the first radiopaque element contacts the tissue while suction is applied through the device.

In at least one embodiment of a device of the present disclosure, the device further comprises one or more optical sensors/electrodes present along the engagement portion and configured to obtain optical data and to transmit the optical data to a console coupled to the device.

In at least one embodiment of a device of the present disclosure, the device further comprises one or more pressure elements/sensors present along a relative inside of the engagement portion and configured to obtain pressure data from within the at least one lumen of the device.

In at least one embodiment of a device of the present disclosure, the device further comprises at least one wire extending from the proximal end of the device to the at least one electrode, the at least one wire configured to transmit data obtained from the at least one electrode through the at least one wire to a console coupled too the device.

In at least one embodiment of a device of the present disclosure, the device further comprises a vacuum gauge mechanism positioned at a proximal end of the device, the vacuum gauge mechanism comprising a movable element configured to move relative to the device when suction is applied through the device.

In at least one embodiment of a device of the present disclosure, the movable element comprises an indication bar having indicia thereon.

In at least one embodiment of a device of the present disclosure, the device comprise an elongated body having a proximal end, a distal end, and at least one lumen extending from the proximal end to the distal end; a compliant suction cup at the distal end of the elongated body, the suction cup configured to engage a tissue adjacent thereto when the engagement portion contacts the tissue while suction is applied through the device; and a bellows adjacent to the suction cup, the bellows configured to move relative to the suction cup when suction is applied through the device;

In at least one embodiment of a device of the present disclosure, the device further comprises at least one electrode present along the engagement portion and configured to contact the tissue when the engagement portion contacts the tissue and to obtain bioimpedance data from the tissue while suction is applied through the device.

In at least one embodiment of a device of the present disclosure, the device further comprises a first radiopaque element present along the suction cup and configured to contact the tissue when the suction cup contacts the tissue.

In at least one embodiment of a device of the present disclosure, the device further comprises a second radiopaque element present along the bellows: wherein the first radiopaque element and the second radiopaque element do not contact one another when no suction is applied through the device; and wherein the first radiopaque element and the second radiopaque element contact one another when suction is applied through the device.

In at least one embodiment of a system of the present disclosure, the system comprises a device, comprising an elongated body having a proximal end, a distal end, and at least one lumen extending from the proximal end to the distal end; an engagement portion at the distal end of the elongated body, the engagement portion configured to engage a tissue adjacent thereto when the engagement portion contacts the tissue while suction is applied through the device; and at least one electrode present along the engagement portion and configured to contact the tissue when the engagement portion contacts the tissue and to obtain bioimpedance data from the tissue while suction is applied through the device; and a needle configured for insertion within at least one lumen of the at least one lumens of the device; wherein when the at least one electrode and the needle contact the tissue, a circuit is created, whereby the circuit is indicative of suction contact of the electrode to the tissue and/or needle contact of the tissue.

In at least one embodiment of a system of the present disclosure, wherein the engagement portion comprises a compliant suction cup; wherein the at least one electrode is present along the suction cup; and wherein the engagement portion further comprises a bellows adjacent to the suction cup, the bellows configured to move relative to the suction cup when suction is applied through the device.

In at least one embodiment of a system of the present disclosure, the system further comprises a first radiopaque element present along the suction cup and configured to contact the tissue when the suction cup contacts the tissue; and a second radiopaque element present along the bellows; wherein the first radiopaque element and the second radiopaque element do not contact one another when no suction is applied through the device; and wherein the first radiopaque element and the second radiopaque element contact one another when suction is applied through the device.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

Figure 1:
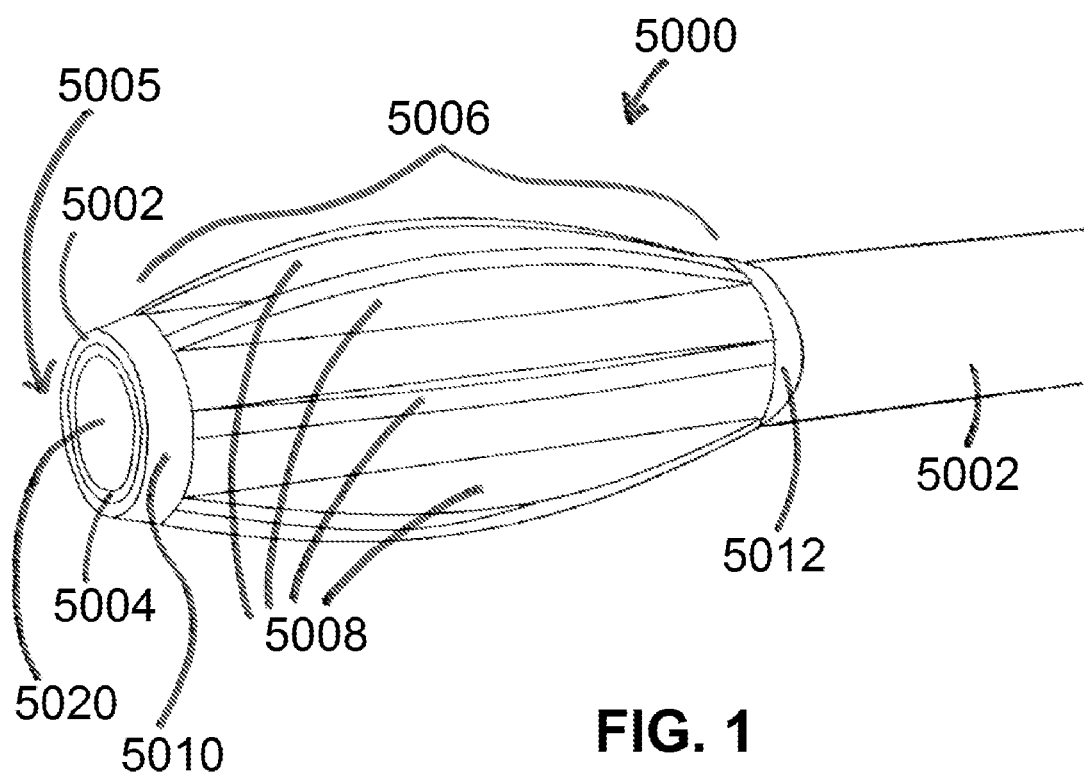
FIG. 1 shows a distal portion of a device configured to form a suction cup in a collapsed configuration, according to an exemplary embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present disclosure includes disclosure of various devices, systems, portions of the same, and methods of using the same, configured so to ensure a user of said devices or systems that said devices or systems have attached to a targeted tissue using suction.

The present disclosure also includes disclosure of a device 5000 useful to facilitate various procedures within or upon a mammalian body or tissue. As shown in FIG. 1, a distal portion of device 500 is shown in a collapsed configuration, which comprises an outer tube 5002 positioned around an inner tube 5004, whereby outer tube 5002 and inner tube 5004 are connected together at a distal end 5005 of device

5000. Device 5000, in various embodiments, further comprises a foldable portion 5006 comprising an optional plurality of flanges 5008, such as arcuate flanges 5008 as shown in the figure. A distal tapered portion 5010 and a proximal tapered portion 5012 may also be included within various device 5000 embodiments.

Figure 2:
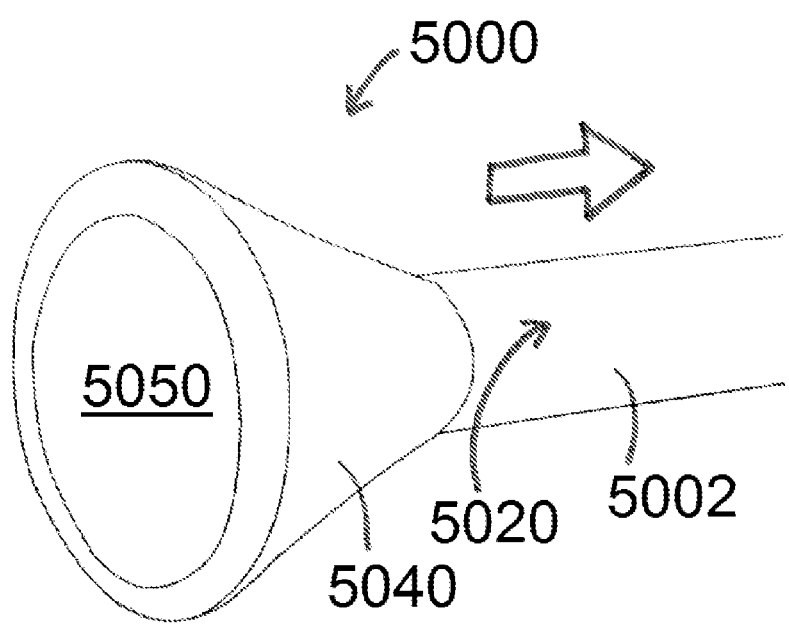
FIG. 2 shows a distal portion of a device configured to form a suction cup in an expanded configuration so to form a suction cup, according to an exemplary embodiment of the present disclosure.

Devices 5000 of the present disclosure are configured to form a suction cup as shown in the expanded configuration of device 5000 shown in FIG. 2, whereby suction cup 5040 is formed by way of relative movement of outer tube 5002 to inner tube 5004. An interior environment 5050, as shown in FIG. 2, is then formed within suction cup 5040. Movement of inner tube 5004 in a proximal direction (as identified by the arrow in FIG. 2) relative to outer tube causes the distal end 5005 of device to fold within itself, whereby distal end 5005 is pulled in the same proximal direction as identified by said arrow. Said movement causes portions of foldable portion 5006 to fold inward (at a now-defined distal end of device 5000), so to form suction cup 5040 as shown in FIG. 2. Device 5000 can be used similar to use of an engagement catheter 1810 of the present disclosure, whereby portions of delivery catheters 1840, needles 1890, wires 1895, etc., can be positioned within an inner lumen 5020 defined within device 5000 (namely the inside of inner tube 5004).

Figure 3:
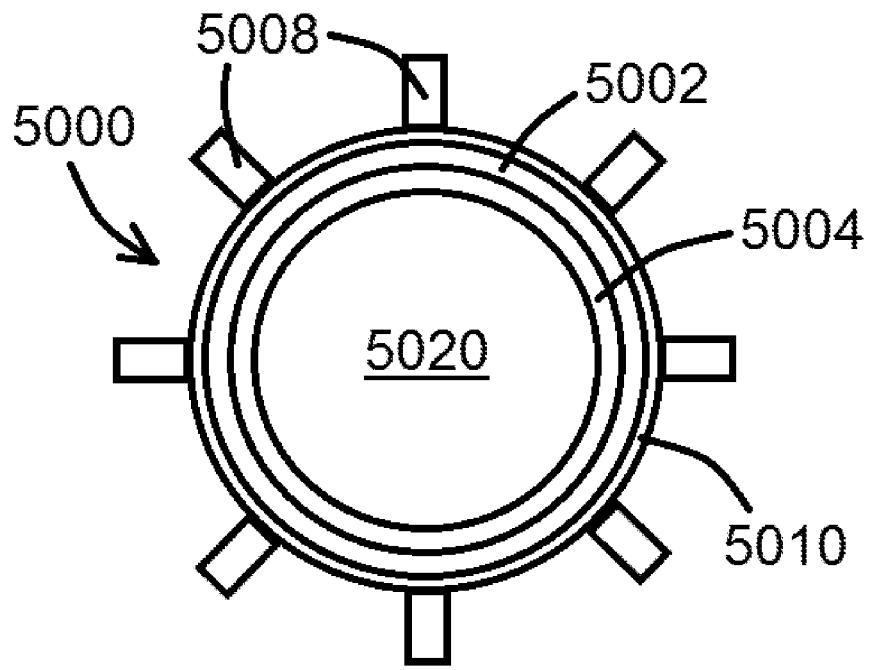
FIG. 3 shows a distal end view of a device configured to form a suction cup in a collapsed configuration, according to an exemplary embodiment of the present disclosure.
Figure 4:
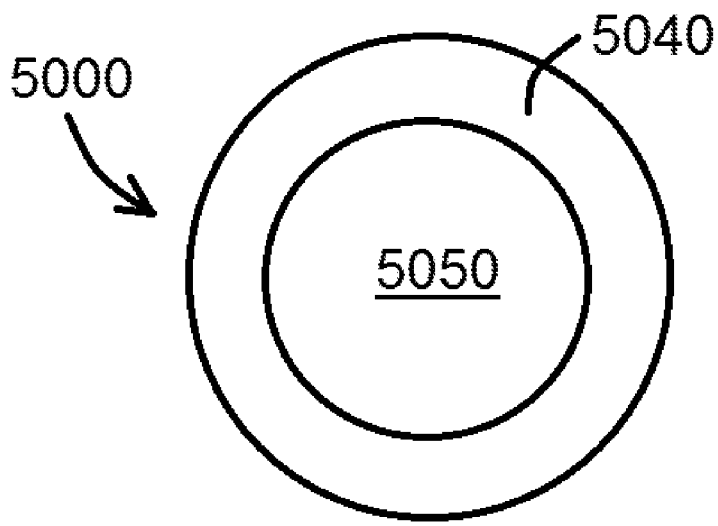
FIG. 4 shows a distal end view of a of a device configured to form a suction cup in an expanded configuration so to form a suction cup, according to an exemplary embodiment of the present disclosure.

Foldable portion 5006, so to be able to form suction cup 5040 (in the collapsed configuration shown in FIG. 2), convert back to foldable portion 5006 (as shown in the expanded configuration shown in FIG. 1), and back to suction cup 5040 (in any order), will comprise a material compliant enough to allow for such folding to occur but to also maintain the shape/integrity of suction cup 5040 when folded over. Flanges 5008, in at least one embodiment, allow for folding and the shape/integrity of suction cup 5040 as referenced herein. Inner tube 5002 and/or outer tube 5004, by way of contrast, may comprise a less compliant (more rigid) material so to allow for suction and/or delivery as referenced herein. Folding of portion 5006 can be adjusted to provide desired sizes and/or shapes of suction cups 5040 based on the degree to which inner tube 5004 is pulled within outer tube 5002 and/or the shape(s) of flanges 5008. The overall shape of suction cups 5040 can be provided by a less compliant material along without requiring flanges 5008 for support. Furthermore, the suction cup 5040 material can be extended to cover an entire movable section (an entire foldable portion 5006), such as shown in FIG. 1, or can extend partially from outer tuber 5002 to provide a desired suction cup 5040 depth and/or shape. FIGS. 3 and 4 show distal end views of embodiments of devices 5000 as described above. Device 5000, in various embodiments, can be considered as being a two-shaft catheter system where the inner, smaller diameter catheter (inner tube 5004) is attached to the distal end of the suction cup 5040 and the outer, larger diameter catheter (outer tube 5002) is attached to the proximal end of the suction cup 5040. Each catheter shaft can move independent of the other. In the collapsed configuration, the inner catheter is extended beyond the outer catheter. In the expanded configuration, the inner catheter is pulled back into the outer catheter causing the suction cup to expand. In various embodiments referenced above, movement of inner tube 5004 relative to outer tube 5002 causes suction cup 5040 to form and/or expand to form the effective foldable portion 5006, noting that folding of foldable portion 5006 is what causes suction cup 5040 to form.

Figure 5:
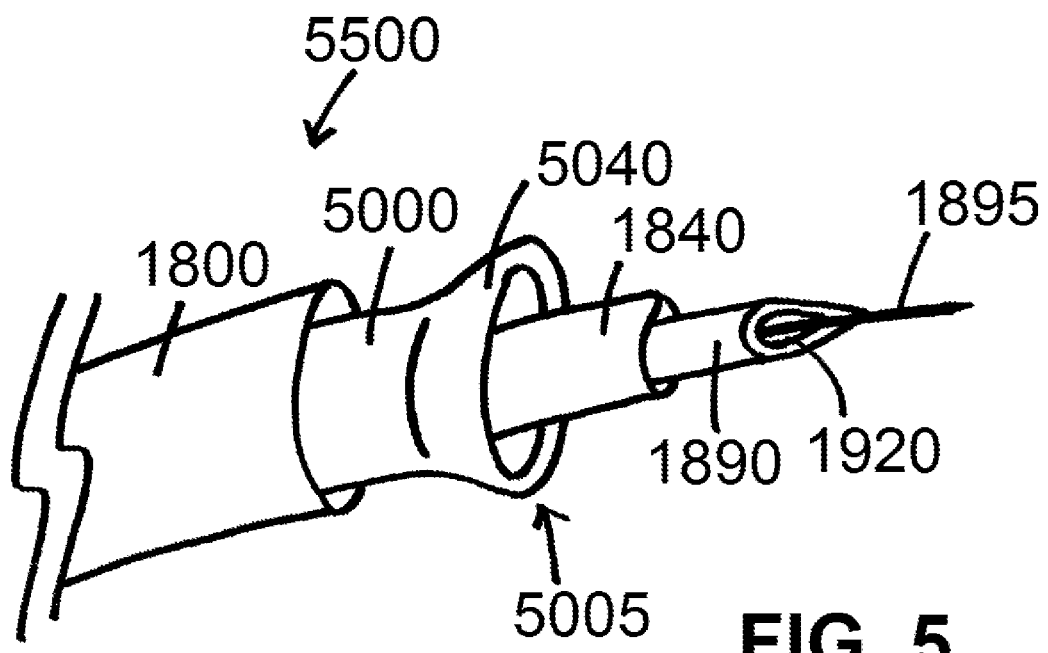
FIG. 5 shows a distal portion of system for isolating tissue and/or delivering a material, according to an exemplary embodiment of the present disclosure.
Figure 6:
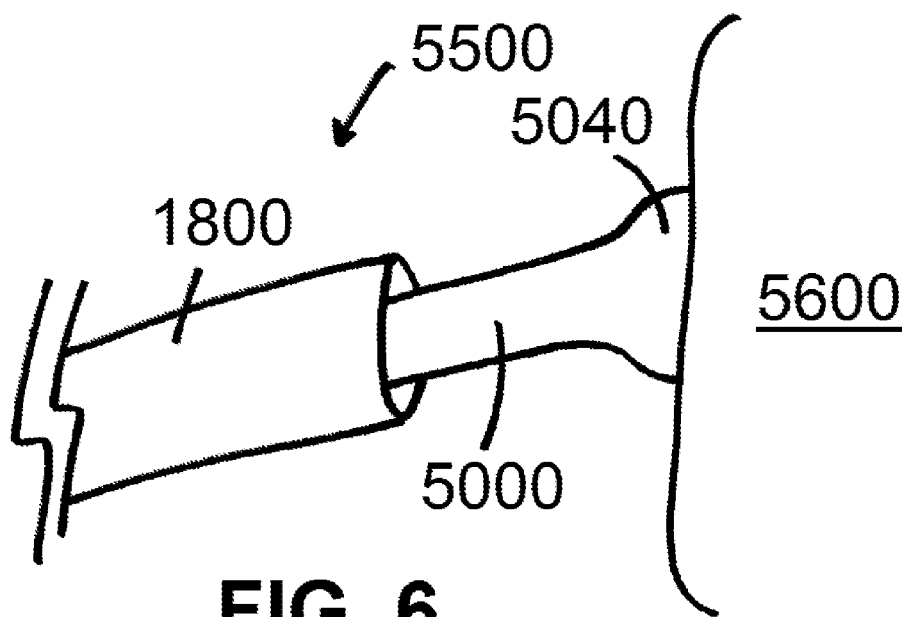
FIG. 6 shows a distal portion of a system suctionally affixed to a mammalian tissue, according to an exemplary embodiment of the present disclosure.
Figure 7:
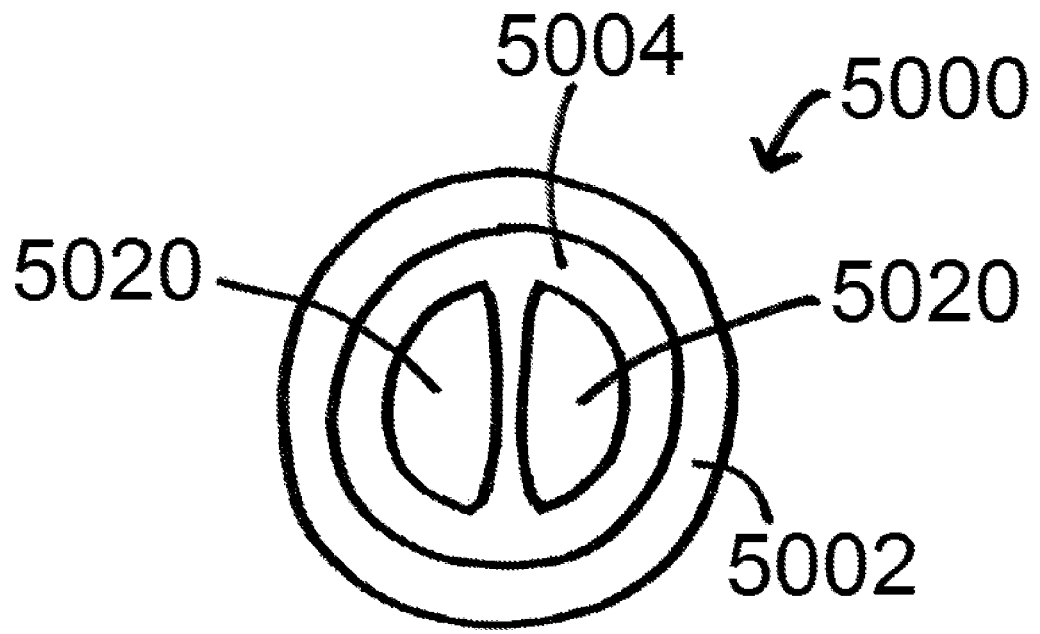
FIGS. 7 and 8 show distal end views of devices, according to exemplary embodiments of the present disclosure.
Figure 8:
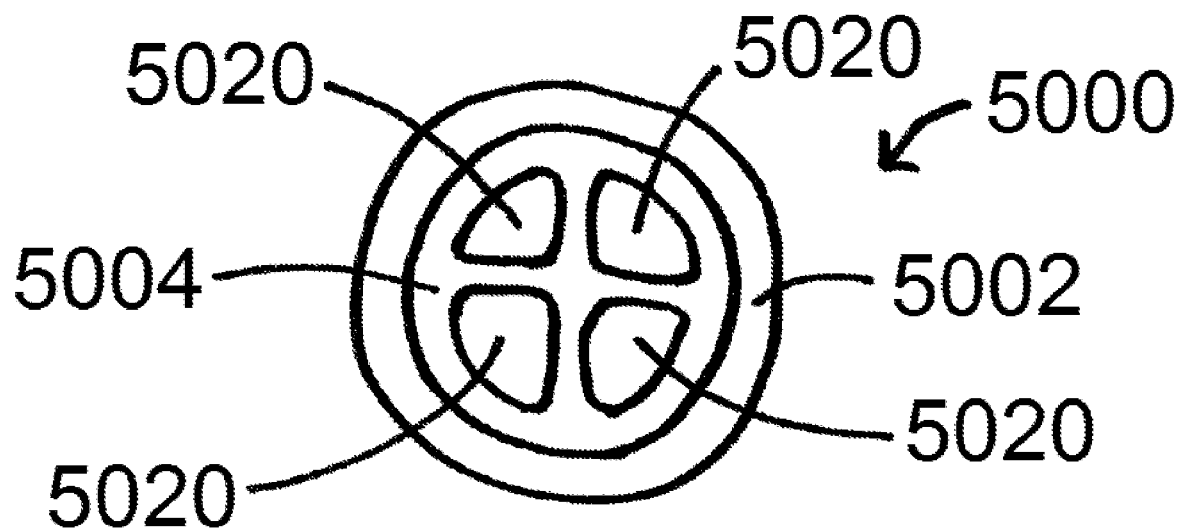

An exemplary system 5500 of the present disclosure is shown in FIG. 5. As shown in FIG. 5, distal portion of an exemplary system 5500 may comprise a device 5000 configured in an expanded configuration so to form a suction cup 5040, as referenced above, at a distal end 5005 of device 5000. System 5000 may further comprise a sleeve 1800 positioned around portions of device 5000 and configured for sliding movement relative to device 5000 such that movement of sleeve 1800 relative to device 5000 can cause suction cup 5040 to be within or external to sleeve 1800. System 5500 may further comprise a delivery catheter 1840 configured to fit within device 5000 and configured for sliding movement relative to device 5000. System 5500 may further comprise a needle 1890 defining a needle aperture 1920 and configured to fit within delivery catheter 1840 and/or device 5000 and configured for sliding movement relative to delivery catheter 1840 and/or device 5000. System 5500 may further comprise a wire 1895 configured to fit within device 5000, delivery catheter 1840, and/or needle 1890, and configured for sliding movement relative to device 5000, delivery catheter 1840, and/or needle 1890. Components of such exemplary system 5500 embodiments may be as described within U.S. Pat. No. 8,328,752 of Kassab et al., the contents of which are expressly incorporated herein by reference. FIG. 6 shows a distal portion of an exemplary system 5500 of the present disclosure, with system 5500 comprising a sleeve 1800 positioned at least partially around a device 5000 configured so to form the suction cup 5040 at a distal end 5005 of device 5000. Suction cup 5040 is shown as engaging a surface of a tissue or organ 5600 (which may be any number of mammalian tissues or organs, such as the skin, a heart, and the like, regardless or a presence of a lumen therein). Such engagement is provided via suction through device 5000. Suction can be provided as described within U.S. Pat. No. 8,328,752 of Kassab et al., noting that various portions of devices and/or systems disclosed within U.S. Pat. No. 8,328,752 of Kassab et al. may be used in connection with devices 5000 and/or systems 5500 of the present disclosure. Various device 5000 embodiments can comprise an inner tube 5004 defining one or more internal lumens 5020 therein. In various embodiments, inner tubes 5004 of the present disclosure may comprise one lumen 5020, as shown in FIG. 1, two internal lumens 5020 as shown in the distal end view of device 5000 shown in FIG. 7, three internal lumens 5020 (not shown), four internal lumens 5020 as shown in the distal end view of device 5000 shown in FIG. 8, or five or more internal lumens 5020. Devices 5000 with multiple lumens 5020 can allow for vacuum, injection, or combinations thereof, as may be required/desired for attachment and delivery of substances, drugs, inert materials, etc., as may be referenced herein, for example.

Figure 9:
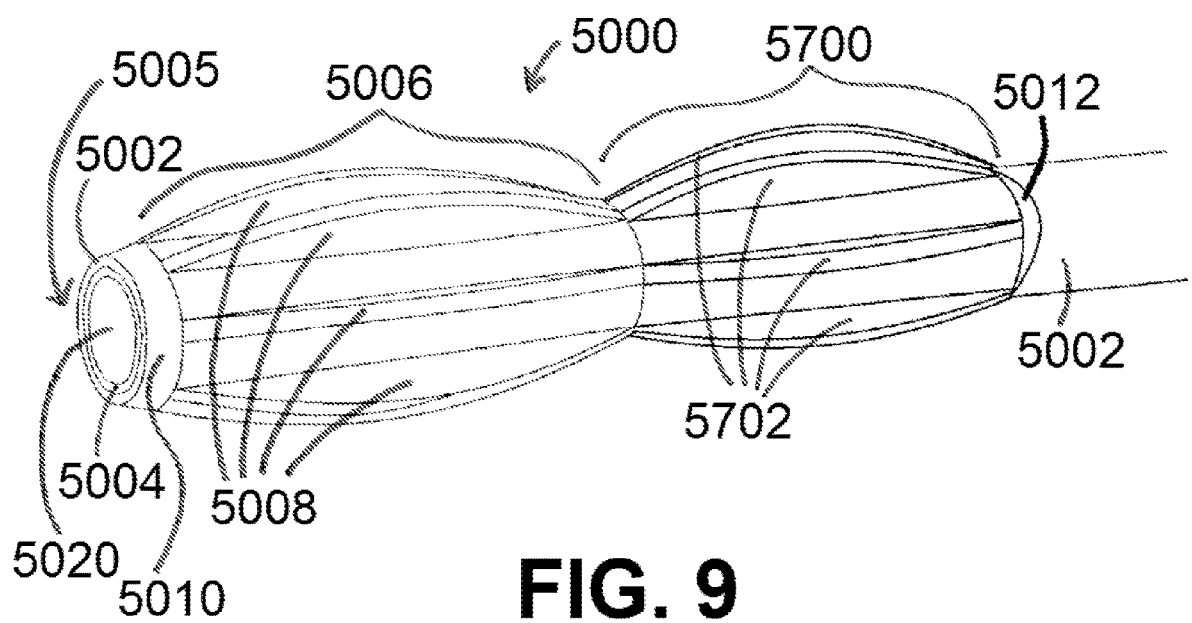
FIG. 9 shows a side perspective view of a distal portion of a device having a foldable portion (configured to fold to form a suction cup) and a foldable bellows portion, in an expanded or unfolded configuration, according to an exemplary embodiment of the present disclosure.
Figure 10:
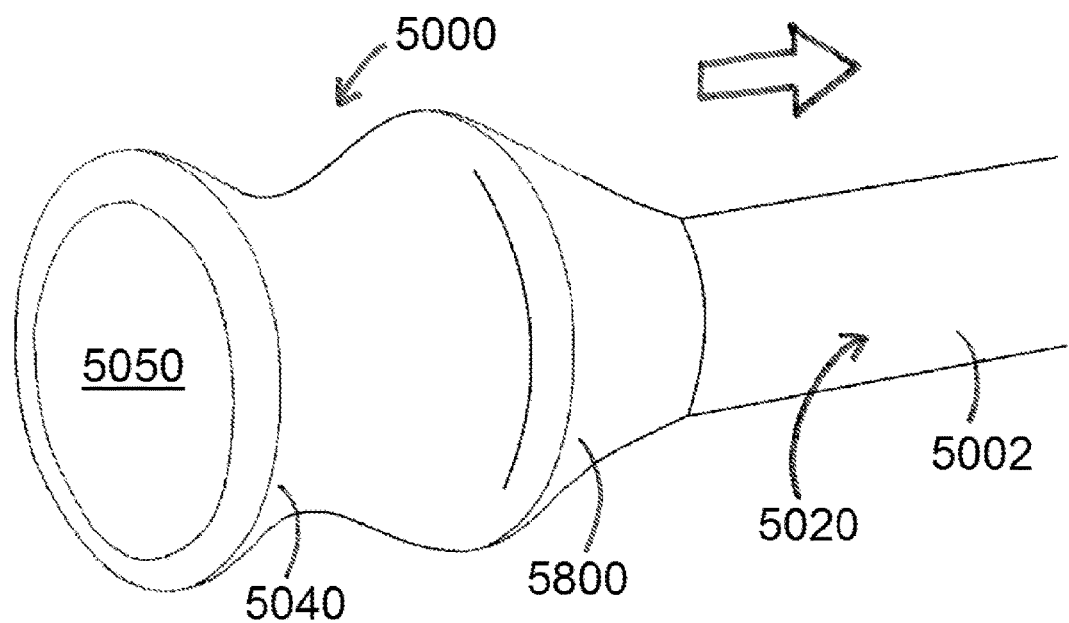
FIG. 10 shows a side perspective view of the device of FIG. 9 in a folded configuration so to form a suction cup and a bellows, according to an exemplary embodiment of the present disclosure.

FIGS. 9 and 10 show an additional embodiment of a device 5000 of the present disclosure. As shown therein, a distal portion of device 500 is shown in a collapsed configuration, which comprises an outer tube 5002 positioned around an inner tube 5004, whereby outer tube 5002 and inner tube 5004 are connected together at a distal end 5005 of device 5000, similar to that as shown in FIG. 1. Device 5000, in various embodiments, further comprises a foldable portion 5006 comprising an optional plurality of flanges 5008, such as arcuate flanges 5008 as shown in the figure. A distal tapered portion 5010 and a proximal tapered portion 5012 may also be included within various device 5000 embodiments. The device 5000 embodiments shown in FIGS. 9 and 10 also include a foldable bellows portion 5700, as shown in FIG. 9. Foldable bellows portion 5700, as shown in FIG. 9, may comprise an optional plurality of bellows flanges 5702, such as arcuate bellows flanges 5702 as shown in the figure. Devices 5000 of the present disclosure are configured to form a suction cup as shown in the expanded configuration of device 5000 shown in FIG. 9, whereby suction cup 5040 is formed by way of relative movement of outer tube 5002 to inner tube 5004. An interior environment 5050, as shown in FIG. 9, is then formed within suction cup 5040. Movement of inner tube 5004 in a proximal direction (as identified by the arrow in FIG. 2) relative to outer tube causes the distal end 5005 of device to fold within itself, whereby distal end 5005 is pulled in the same proximal direction as identified by said arrow. Said movement causes portions of foldable portion 5006 to fold inward (at a now-defined distal end of device 5000), so to form suction cup 5040 as shown in FIG. 9. Said movement also causes portions of foldable bellows portion 5700 to fold inward, so to form a bellows 5800, as shown in FIG. 10. Bellows 5800, as shown in FIG. 10, is proximal to suction cup 5040. FIGS. 9 and 10 show one foldable bellows portion 5700 and one bellows 5800, respectively, but in various other device 5000 embodiments, two, three, or more bellows portions 5700, corresponding to two, three, or more bellows 5800 when folded, may be present.

Foldable portion 5006, so to be able to form suction cup 5040, and foldable bellows portion 5700, so to be able to form bellows 5800 (in the collapsed configuration shown in FIG. 10), convert back to foldable portion 5006 and foldable bellows portion 5700 (as shown in the expanded configuration shown in FIG. 9), and back to suction cup 5040 and bellows 5800 (in any order), will comprise a material compliant enough to allow for such folding to occur but to also maintain the shape/integrity of suction cup 5040 and bellows 5800 when folded over. Flanges 5008 and 5702, in at least one embodiment, allow for folding and the shape/integrity of suction cup 5040 and bellows 5800 as referenced herein, Inner tube 5002 and/or outer tube 5004, by way of contrast, may comprise a less compliant (more rigid) material so to allow for suction and/or delivery as referenced herein.

Figure 11:
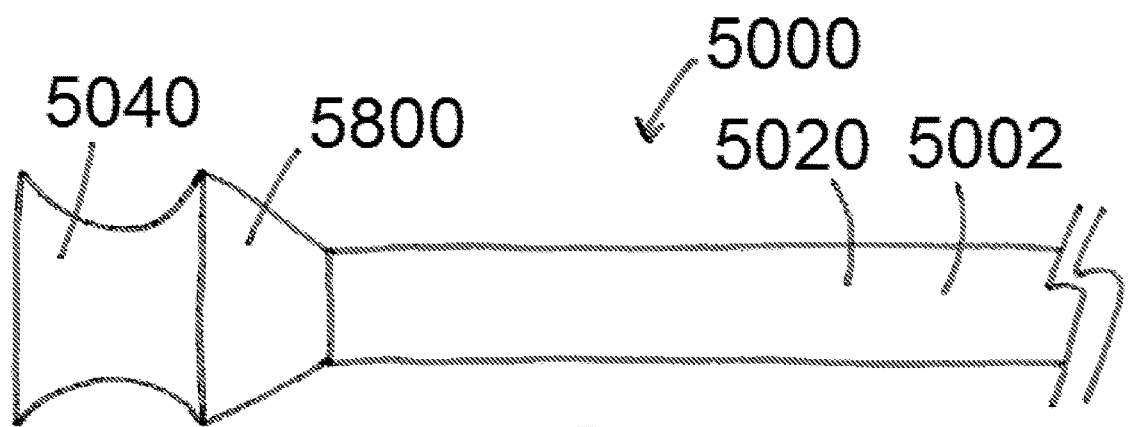
FIG. 11 shows a side view of a device having a suction cup and a bellows, according to an exemplary embodiment of the present disclosure.
Figure 12:
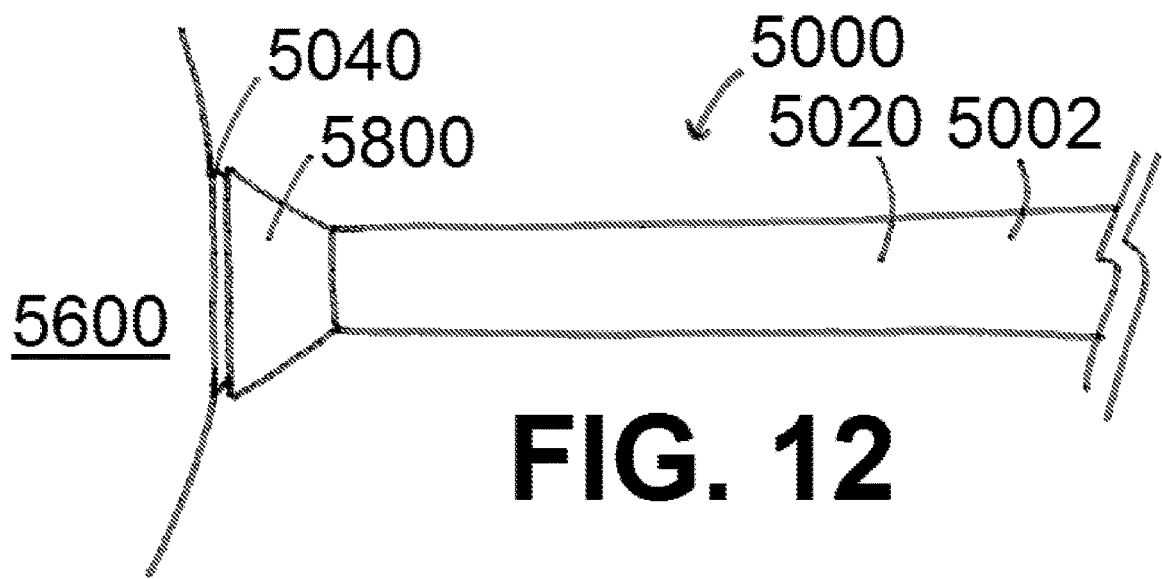
FIG. 12 shows a side view of a device whereby the bellows is folded about/upon the suction cup under suctional attachment to a tissue, according to an exemplary embodiment of the present disclosure.

An additional device 5000 embodiment of the present disclosure is shown in FIGS. 10 and 11. As shown therein, devices 5000 comprise a suction cup 5040 and at least one bellows 5800 proximal to said suction cup 5040, similar to as shown in FIG. 10. Suction cup 5040 and bellows 5800 are configured so that when no vacuum is applied through device 5000 (meaning here that there is no meaningful vacuum present within device 5000), bellows 5800 remains expanded, as shown in FIG. 11, and when vacuum is applied through device 5000 (meaning here that there is meaningful vacuum present within device 5000, such as when suction cup 5040 is suctionally attached to a targeted tissue 5600), bellows 5800 collapses about/upon suction cup 5040, as shown in FIG. 12. In view of the foregoing, the present disclosure includes disclosure of a suction engagement catheter (an exemplary device) having one, two, three, or more bellows 5800 proximal to a distal suction cup 5040, whereby, during application of suction and tissue engagement, the one, two, or three or more bellows 5800 collapse about one other.

Figure 13:
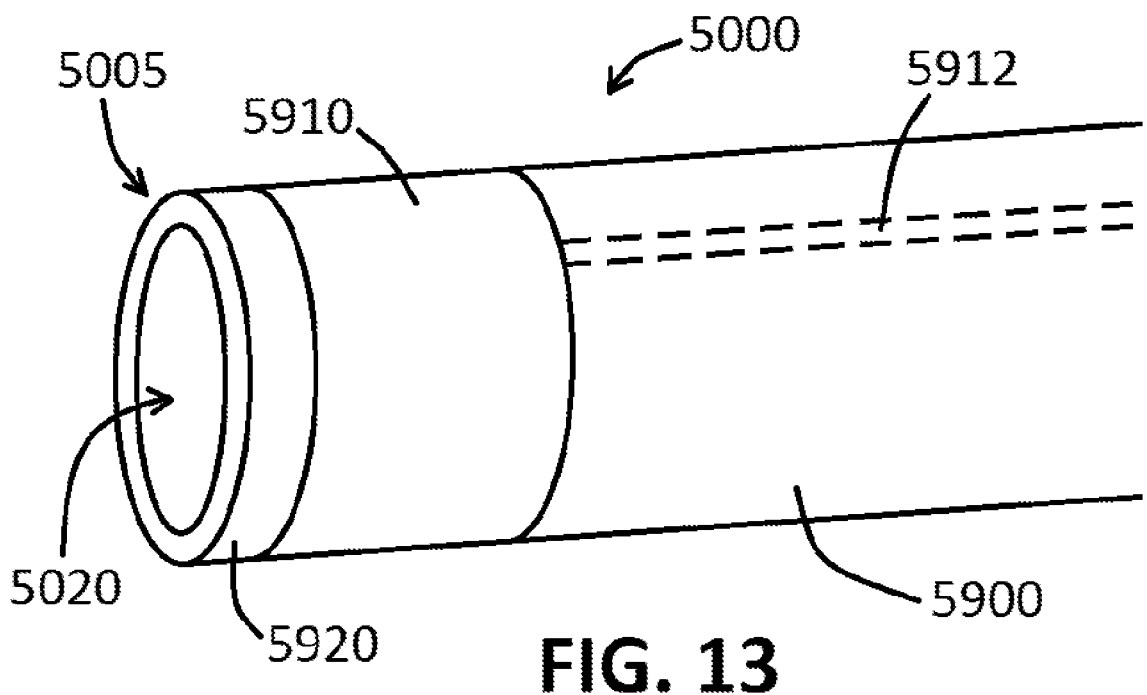
FIGS. 13 and 14 show perspective views of devices having a balloon in a deflated state, according to exemplary embodiments of the present disclosure.
Figure 14:
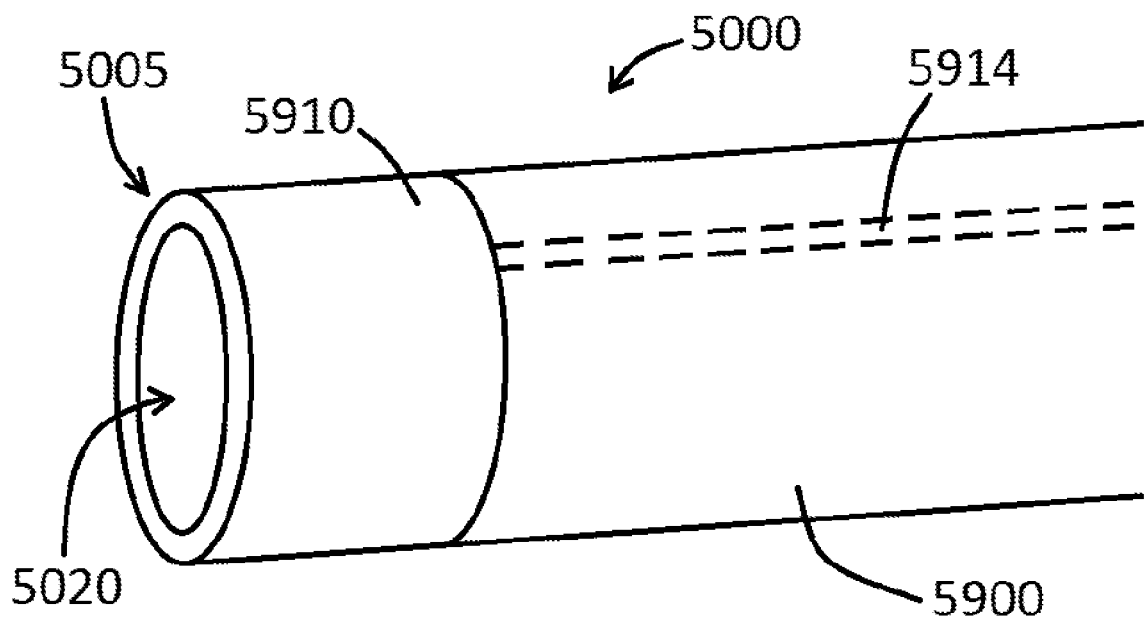
Figure 15:
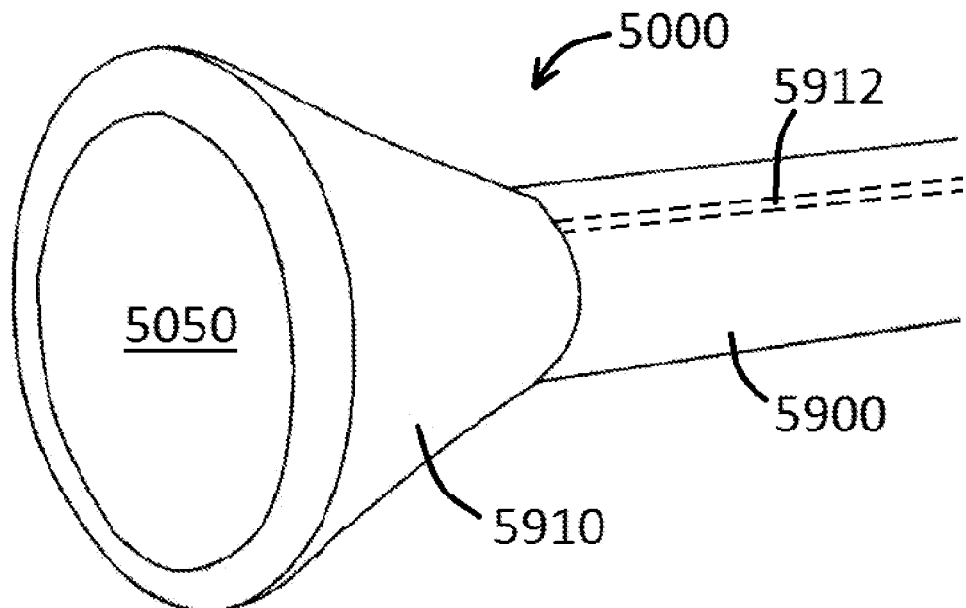
FIG. 15 shows a perspective view of a device having a balloon shaped as a funnel in an inflated state, according to an exemplary embodiment of the present disclosure.
Figure 16:
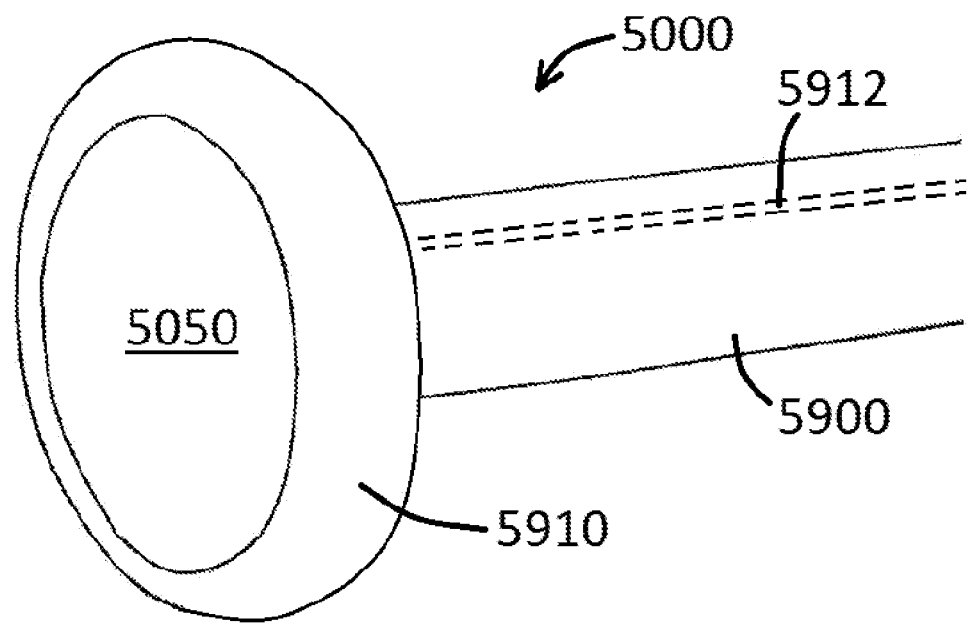
FIG. 16 shows a perspective view of a device having a balloon shaped as a donut in an inflated state, according to an exemplary embodiment of the present disclosure.
Figure 19:
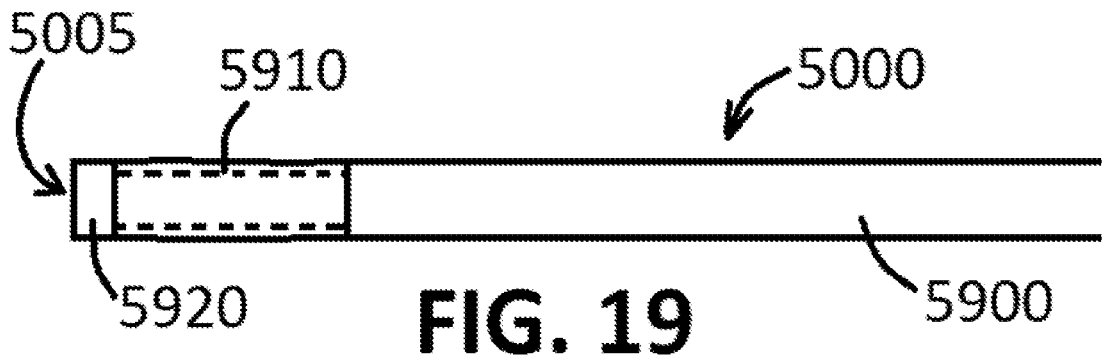

FIG. 13 shows an additional embodiment of a device 5000 of the present disclosure. As shown therein. Device 5000 comprises an elongated body 5900 configured as a catheter, whereby elongated body 5900, in various embodiments, could comprise outer tube 5900. Device 5000, as shown in FIG. 13, comprises a balloon 5910 positioned at or near a distal end 5005 of device. Balloon 5910, as shown in FIG. 13, is positioned along device 5000 proximal to distal end 5005, whereby a distal tube element 5920 is present between distal end 5005 and the rest of elongated body 5000. In other embodiments, such as shown in FIG. 14, balloon 5900 is positioned along device 5000 at distal end 5005 of device, such that no distal tube element 5920 is present. Balloon 5910, as shown in FIG. 13, is configured for inflation via an inflation port 5912 defined within elongated body 5900, or as shown in FIG. 14, via an inflation tube 5914 positioned relative to elongated body 5900. Balloon 5910, in an inflated state (such as shown in FIGS. 15 and 16), can have a funnel shape, such as shown in FIG. 15, or a donut shape, such as shown in FIG. 16, for example. Balloon 5910 can also be configured as a bellows 5800, such as shown in FIG. 10, upon inflation. Inflation of balloon 5910 can occur by way of operating an inflation source 6102 coupled to device 5000, such as to supply a gas and/or a liquid to inflate balloon 5910, via inflation port 5912 or inflation tube 5914 in communication with inflation source. Balloon 5910, when inflated, defines an interior environment 5050, whereby at least part of interior environment 5050 is sized so to have a diameter larger than a diameter of device 5000 or to have a cross-sectional area larger than a cross-sectional area of device 500. For example, and as shown in the end view of device 5000 shown in FIG. 19, inflated balloon 5910 has a distal opening having an inner diameter D1, as shown in the figure, while elongated body 5900 (configured as a tube, for example) has an inner diameter D2, as shown in the figure. D1, as shown in FIG. 19, is larger than D2. Use of such a device 5000, such as to engage a tissue or organ 5600, allows for a larger surface area of tissue or organ 5600 contact as compared to potential tissue contact with only elongated body 5900, when suction (vacuum) is applied through lumen 5020 of device, as referenced herein. The engagement of the larger surface area of the tissue or organ 5600 under vacuum allows device 5000 to better adhere to said tissue or organ 5600 under vacuum.

Figure 17:
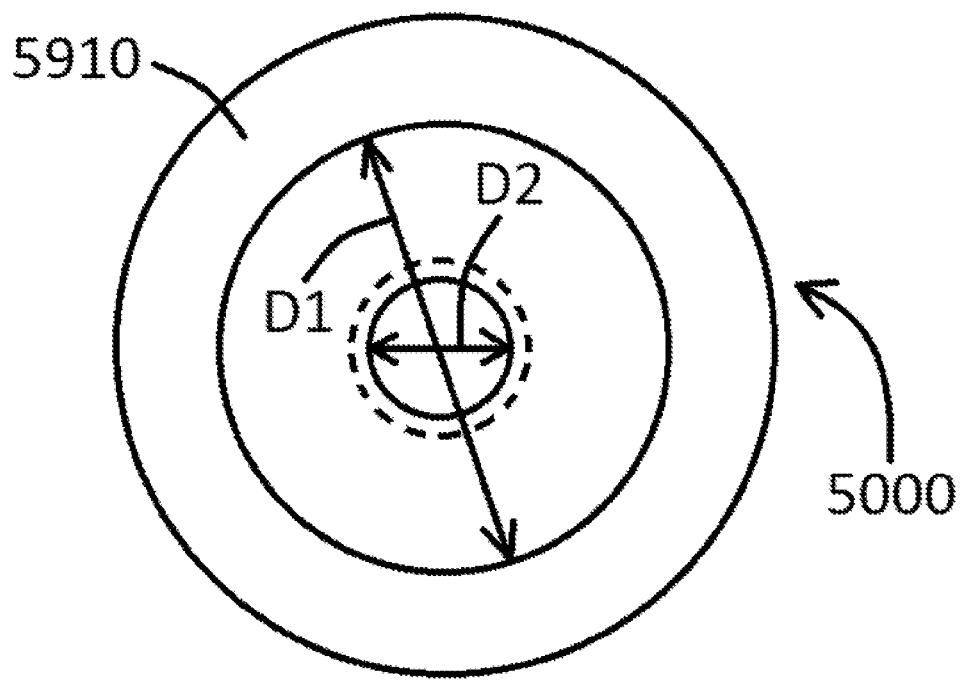
FIG. 17 shows an end view of a device having a balloon in an inflated state, according to an exemplary embodiment of the present disclosure.
Figure 18:
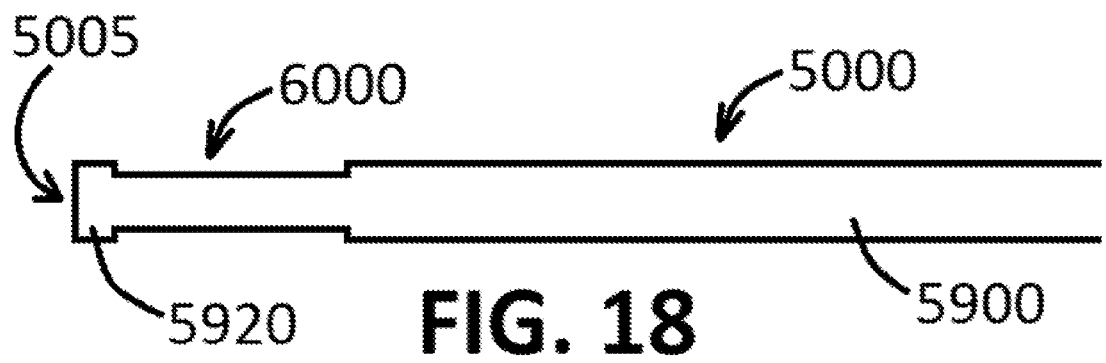
FIGS. 18, 19, 20, and 21 show side views of devices having a notch or groove defined therein, according to exemplary embodiments of the present disclosure.
Figure 20:
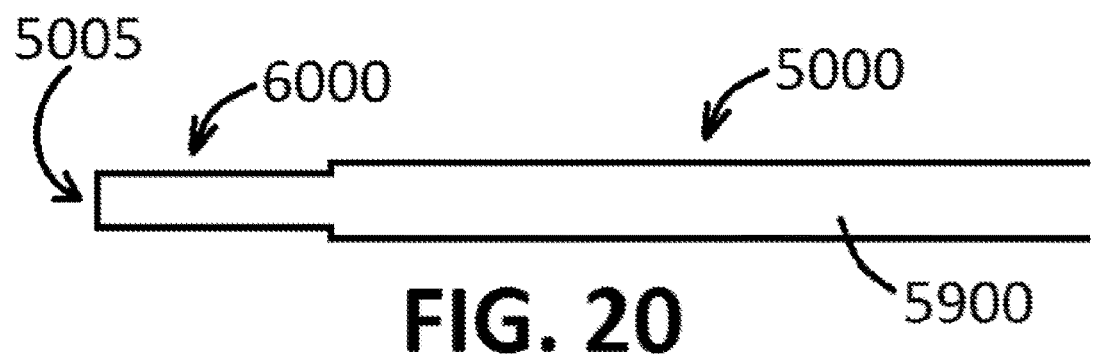
Figure 21:
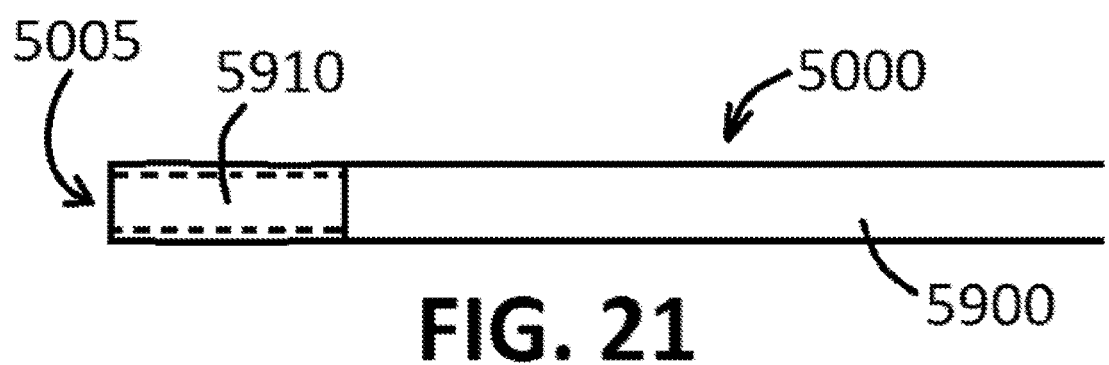

FIG. 18 shows an exemplary side view of a distal portion of a device 5000 of the present disclosure. As shown therein, a notch or groove 6000 is defined within elongated body at or near distal end 5005, whereby balloon 5910 can be positioned at notch or groove 6000, such as shown in FIG. 19. Balloon 5910, in a deflated state, allows device 5000 to be delivered via the vascular system as desired, and inflation of balloon 5910, such as shown in FIGS. 15, 16, and 17, provides for a larger cross-sectional area for tissue or organ 5600 engagement under vacuum, as referenced herein. Notch or groove 6000 can be defined within elongated body 5900 near distal end 5005 of device 5000, such as shown in FIGS. 18 and 19, or can be defined at distal end 5005 of device 5000, such as shown in FIGS. 20 and 21. Devices 5000, as referenced herein, can be exemplary engagement catheters 1810 of the present disclosure, as devices 5000 can be used to attach to a targeted tissue or organ 5600 under vacuum, as referenced herein and as shown in FIG. 6, for example.

Figure 22:
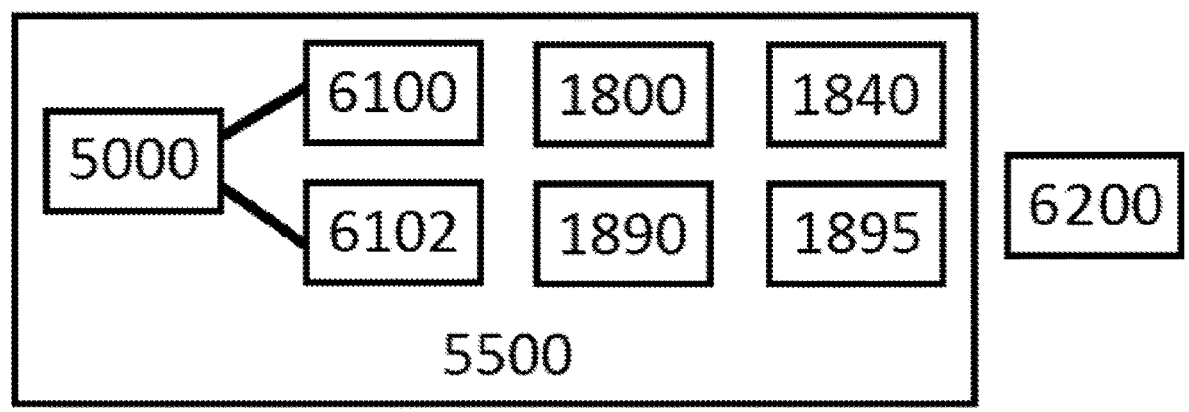
FIG. 22 shows a block component diagram of a system, according to an exemplary embodiment of the present disclosure.

FIG. 22 shows a block component diagram of an exemplary system 5500 of the present disclosure. As shown therein, system 5500 comprises an exemplary device 5000 of the present disclosure, coupled to a vacuum source 6100 (configured to generate a vacuum within lumen 5020 of device 5000 to facilitate suction engagement to a tissue or organ 5600), and also coupled to an inflation source 6102 (configured to inflate balloon 5910 using a gas and/or a liquid). Systems 5500 can include one or both of vacuum source 6100 and/or inflation source 6102, and can include/comprise one or more of a sleeve 1800, a delivery catheter 1840, a needle 1890, and/or a wire 1895, as shown and/or described herein. In various device 5000 embodiments, the one or more bellows 5800 provide articulation to device 500, such as to, for example, allow a device 5000 configured as a catheter to be better controlled during intravascular navigation, for example, as well as to provide for a more accurate and controlled delivery of a needle 1890 and/or media (such as one or more materials referenced herein).

Procedurally, portions of devices 5000 and/or systems 5500 can be delivered subendocardially, such as by way of needle puncture, so that suction cup 5500 is ultimately positioned against tissue or organ 5600 as desired. Various devices 5000 and/or portions of systems 1805 of the present disclosure can be delivered intravascularly, via thoracic puncture, etc., for ultimate use within the body, or can be used external to the body, such as upon the skin. Devices 5000 and/or systems 5500 can be used as follows, by way of example: a) to suctionally engage a tissue or organ 5600 so to stabilize said tissue or organ 5600; and/or b) to suctionally engage a tissue or organ 5600 so to directly deliver an item 6200 such as, for example, a medicament, such as a pharmaceutical compound (a drug), an injectable material, such as a polymer, a lead, cells, a coil, and/or another medical device; and/or c) to suctionally engage a tissue or organ 5600 so to facilitate delivery of a delivery catheter 1840, a needle 1890, and/or a wire 1920 through device 5000, whereby said delivery catheter 1840 and/or needle 1890 can be used to deliver an item 6200 such as, for example, a medicament, such as a pharmaceutical compound, an injectable material, a lead, a coil, and/or another medical device, and/or whereby wire 1920 can be used to guide portions of device 5000 and/or system 5500 within the body. Other uses of exemplary devices 5000 and/or systems 5500 are also contemplated herein and within the present disclosure, such as during known or developed medical procedures whereby suction engagement of a catheter to a tissue or organ 5600 is part of the procedure.

As referenced herein, various device embodiments are configured so to be able to sense suction engagement with a tissue of interest, such as a myocardium or other mammalian tissue, while portions of devices are positioned intravascularly or otherwise within a patient. Confirmation of suction engagement is important as if a therapeutic substance, such as a drug, a stem cell, a polymer, etc., is delivered through the device (directly or via needle, for example), a user of said device would want to ensure that the therapeutic substance is properly delivered, such as into the tissue of interest, and that it is not embolized in a ventricle and/or does not otherwise flow/spread throughout the body and embolized there.

Figure 23:
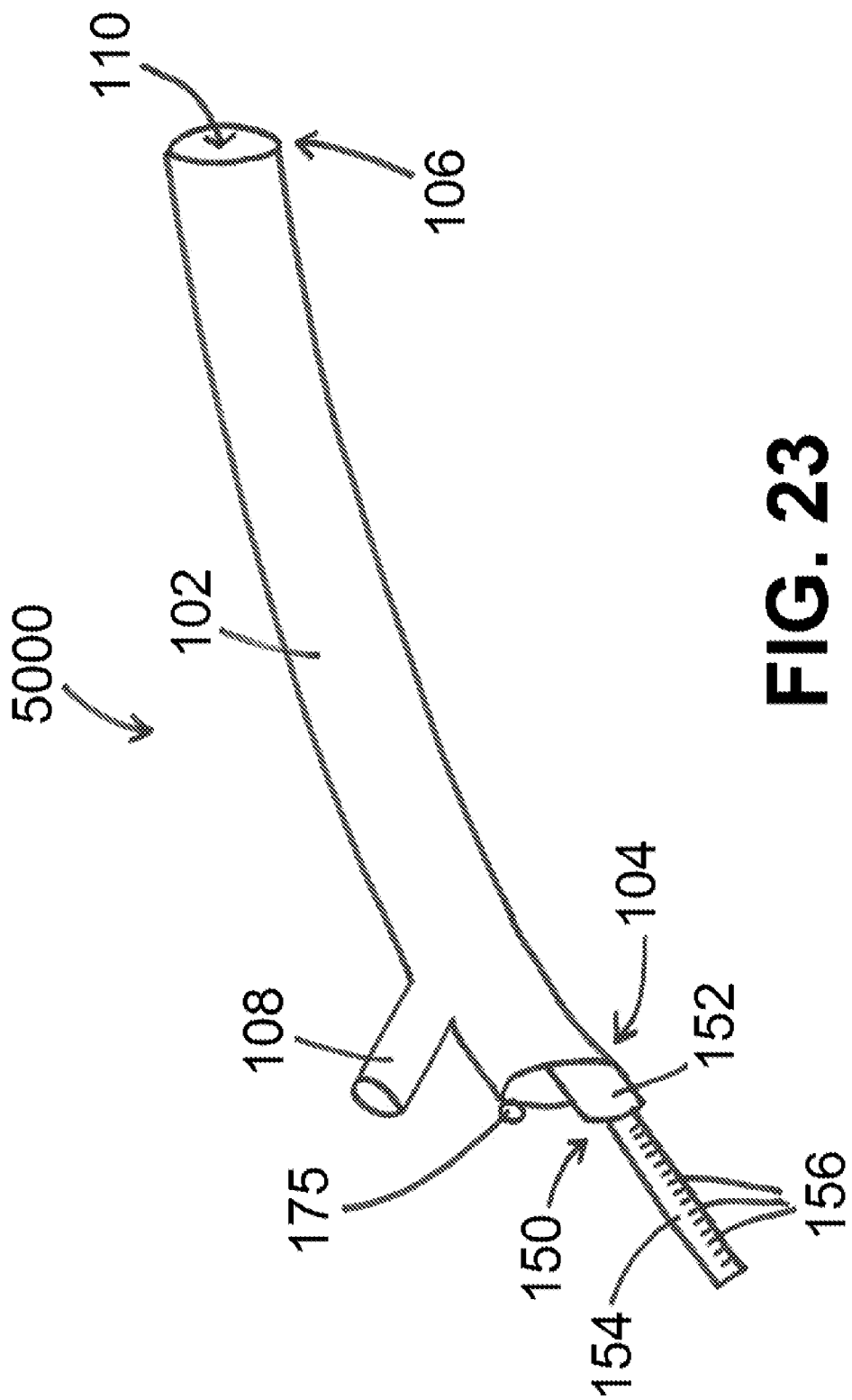
FIG. 23 shows a side perspective view of a device, according to an exemplary embodiment of the present disclosure.

An exemplary device 5000 of the present disclosure is shown in FIG. 23. As shown therein, device 5000, in an exemplary embodiment, is configured as a catheter and comprises an elongated body 5900 defining a proximal end 104 and a distal end 106. A vacuum gauge mechanism 150, as shown therein, is positioned at or near proximal end 104, such as between proximal end 104 and a vacuum port 108 located at or near proximal end 104 (or at least at a relative proximal half (versus a distal half)) of device 5000, and comprises at least one movable element 152, such as a spring (or spring-like mechanism) or a needle. Upon application of negative pressure (vacuum) through a lumen 110 of device, such as by way of operation of a vacuum source 6100 (not shown in FIG. 23, but shown in FIG. 24) operably coupled to vacuum port 108 of device 5000, movable element 152 would physically move when distal end 106, or an element of device 5000 located at or near distal end 106, suctionally adheres to a targeted tissue. Movable element 152 may be or further comprise an indication bar 154 having indicia 156 thereon, whereby indicia 156 (tick marks, numbers, letters, colors, etc.) exist along indication bar 154 and provide a user with a visual guide as to the potential extent of vacuum within device 5000. A higher extent of vacuum may then be indicated by the extent of movement of movable element 152 and/or indication bar 154 as compared to no or less vacuum. In use, for example, vacuum present within lumen 110 of device 5000 would be indicated by movable element 152 and/or indication bar 154 as being low, lower, or relatively low when distal end 106 is not suctionally adhered to a tissue of interest, and vacuum present within lumen 110 of device 5000 would be indicated by movable element 152 and/or indication bar 154 as being high, higher, or relatively higher when distal end 106 is suctionally adhered to a tissue of interest.

Figure 24:
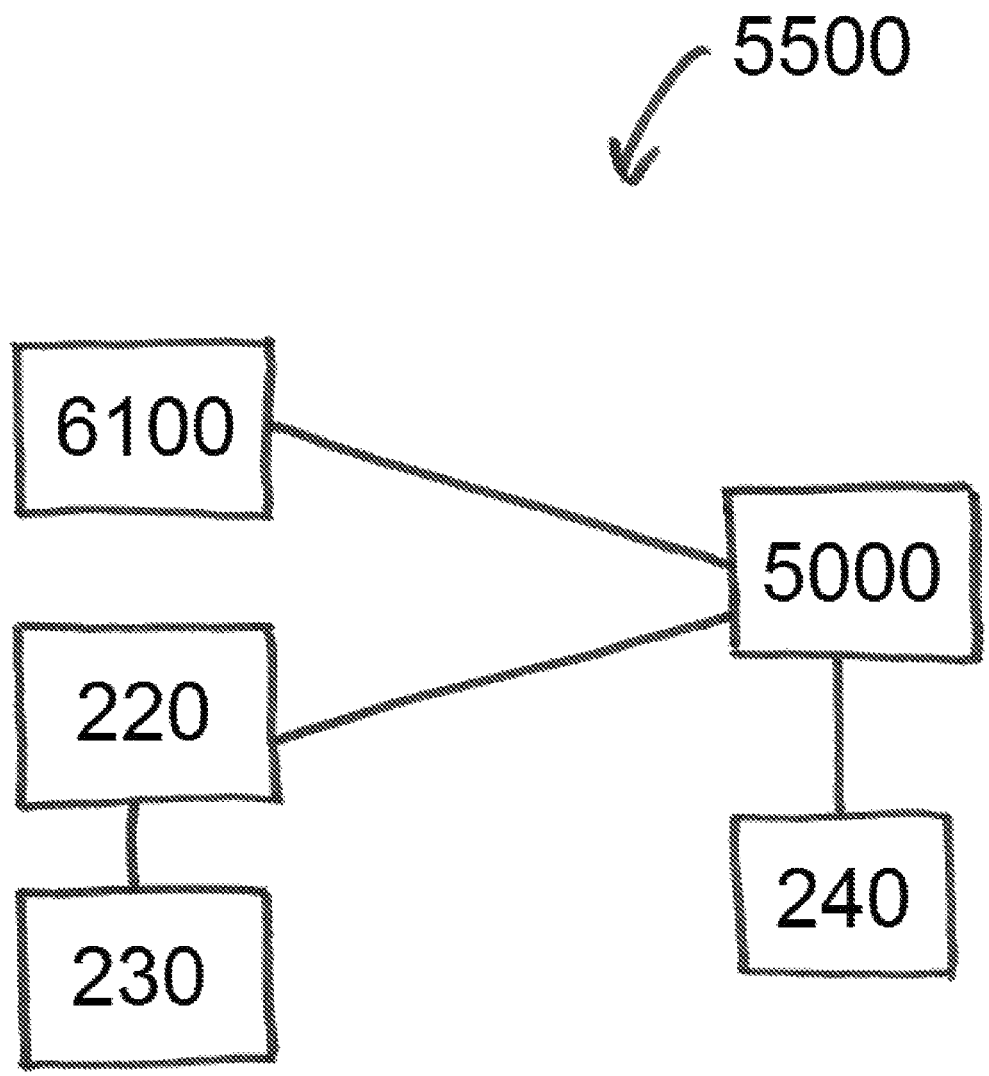
FIG. 24 shows a block component diagram of elements of a system, according to an exemplary embodiment of the present disclosure.

FIG. 24 shows an exemplary system 200 of the present disclosure, comprising an exemplary device 5000, a vacuum source 6100, and an injection source 220, whereby injection source 220 is operable to deliver a substance 230 into device 5000 and to a targeted tissue of interest. Exemplary systems 200 of the present disclosure may further comprise a console 240, such as a computer having a processor and a storage medium, with software/programs/instructions stored on said storage medium and operable using said processor to direct operation of console 240, as known or developed.

Figure 25:
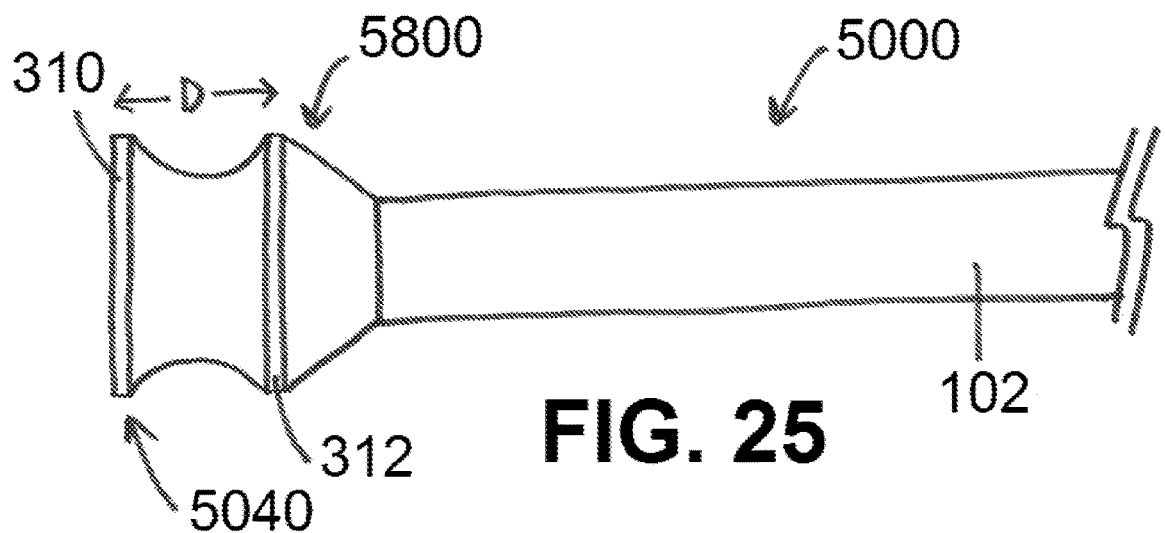
FIG. 25 shows a side view of a device having an expanded bellows, according to an exemplary embodiment of the present disclosure.
Figure 26:
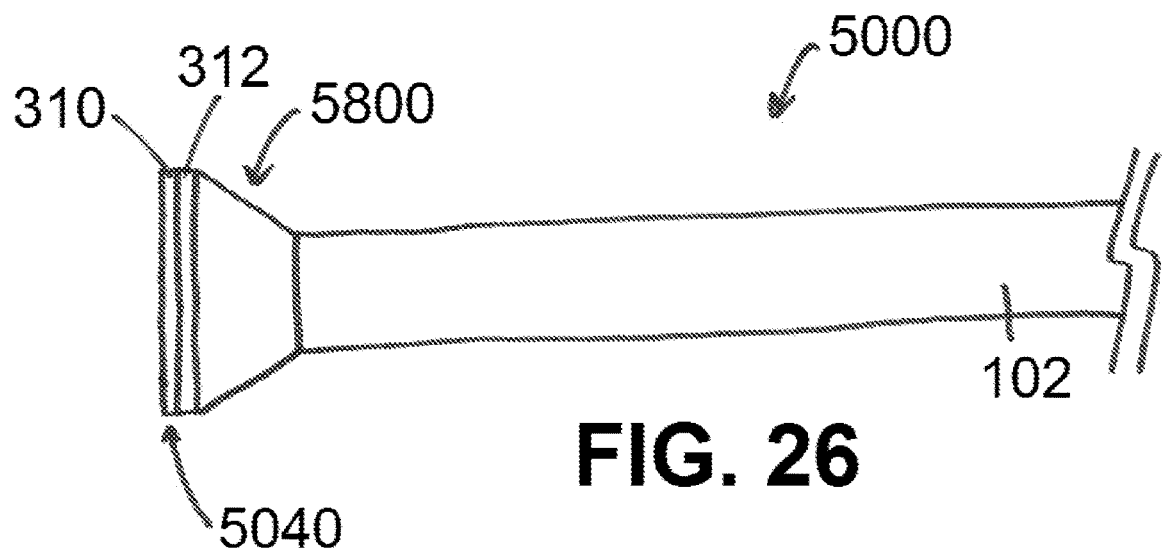
FIG. 26 shows a side view of a device having a collapsed bellows, according to an exemplary embodiment of the present disclosure.

An additional device 5000 embodiment of the present disclosure is shown in FIGS. 25 and 4. As shown therein, devices 5000 comprise a distal suction cup 5040 and at least one bellows 5800 proximal to said suction cup 5040. Suction cup 5040 and bellows 5800 are configured so that when no vacuum is applied through device 5000 (meaning here that there is no meaningful vacuum present within device 5000), bellows 5800 remains expanded, as shown in FIG. 25, and when vacuum is applied through device 5000 (meaning here that there is meaningful vacuum present within device 5000, such as when suction cup 5040 is suctionally attached to a targeted tissue), bellows 5800 collapses about/upon suction cup 5040, as shown in FIG. 26. In view of the foregoing, the present disclosure includes disclosure of a suction engagement catheter (an exemplary device) having one, two, three, or more bellows 5800 proximal to a distal suction cup 5040, whereby, during application of suction and tissue engagement, the one, two, or three or more bellows 5800 collapse about one other.

Devices 5000 of the present disclosure may comprise a first radiopaque element 310 positioned at, along, or within suction cup 5040, and a second radiopaque element 312 positioned at, along, or within bellows 5800, as shown in FIGS. 25 and 26. Elements 310, 312 may be radiopaque rings, portions thereof, wires, dots, etc., as desired, but would appear under x-ray or another scanning mechanism, for example. Elements 310, 312 are shown as radiopaque rings in FIGS. 25 and 26. Radiopaque elements 310, 312 may also be any of an electrode 500, an optical element/sensor 900, and/or a pressure element/sensor 910, as described in further detail herein.

Said elements 310, 312 would initially be spaced apart by a distance "D" as shown in FIG. 25. Upon application of vacuum through device 5000 when suction cup 5040 is adjacent to a tissue, suction cup 5040 would suctionally engage said tissue, and elements 310, 312 would move toward one another, so to be adjacent to one another, as shown in FIG. 26. Said movement and/or positioning could be readily identified under x-ray or another scanning mechanism, for example, and would indicate whether or not suction cup 5040 is suctionally attached to said tissue. One interpretation of the differences between FIGS. 25 and 26 would be that the two elements 310, 312 shown in FIG. 25 effectively collapse into one, given that elements 310, 312 would be immediately or relatively adjacent to one another when effective vacuum is applied as shown in FIG. 26.

Figure 27:
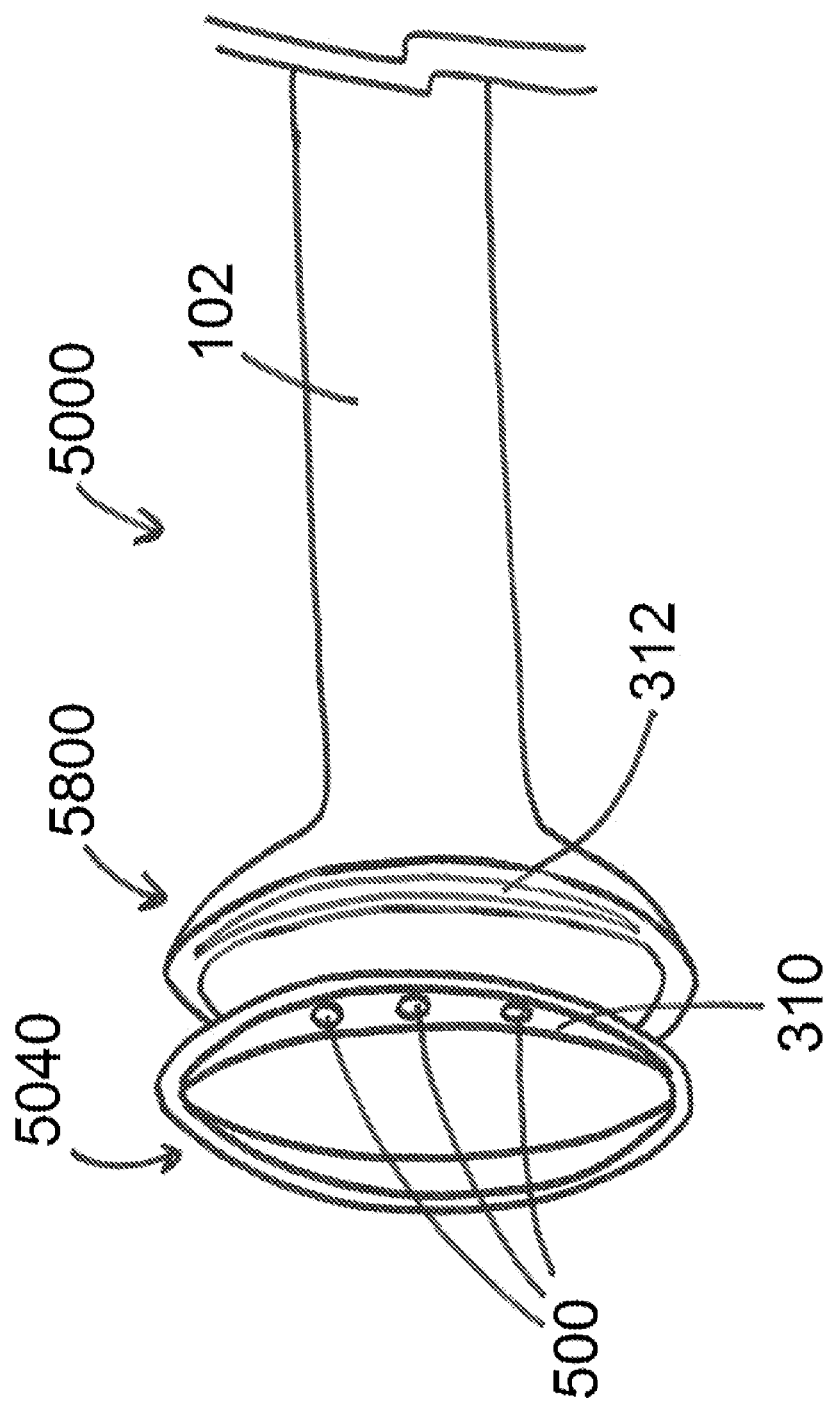
FIG. 27 shows a side perspective view of a device having electrodes thereon, according to an exemplary embodiment of the present disclosure.

FIG. 27 shows a perspective view of a portion of a device 5000 whereby radiopaque elements 310, 312 (of suction cup 5040 and bellows 310, respectively), are readily apparent. An exemplary device 5000 of the present disclosure, such as shown in FIG. 27, may further comprise one or more electrodes 500 along/on/at suction cup 5040, configured to obtain impedance/conductance data (also referred to as bioimpedance data) using conductance when operated. One or more electrodes 500 may be operable to obtain impedance/conductance data when suction cup 5040 is not suctionally engaged to a tissue and when suction cup 5040 is suctionally engaged to said tissue. Changes in impedance/conductance would indicate engagement. Furthermore, and for example, when a metallic element (such as a needle, referenced in further detail below) positioned within device 5000 contacts the same tissue that suction cup 5040 is suctionally engaged to, additional changes in impedance/conductance could be identified, as for example, an overall circuit comprising electrodes 500 and said needle would be completed through said tissue, causing the impedance/conductance data changes. Said data could be transferred through device 5000 to a console 240 operably coupled to device 5000, whereby console 240 could process said data and indicate to a user of device 5000 that suction engagement has been achieved. An indicator light 175, such as shown in FIG. 22, positioned at or near proximal end 104 of device 5000, could also illuminate and/or change color to indicate suction engagement.

Figure 28:
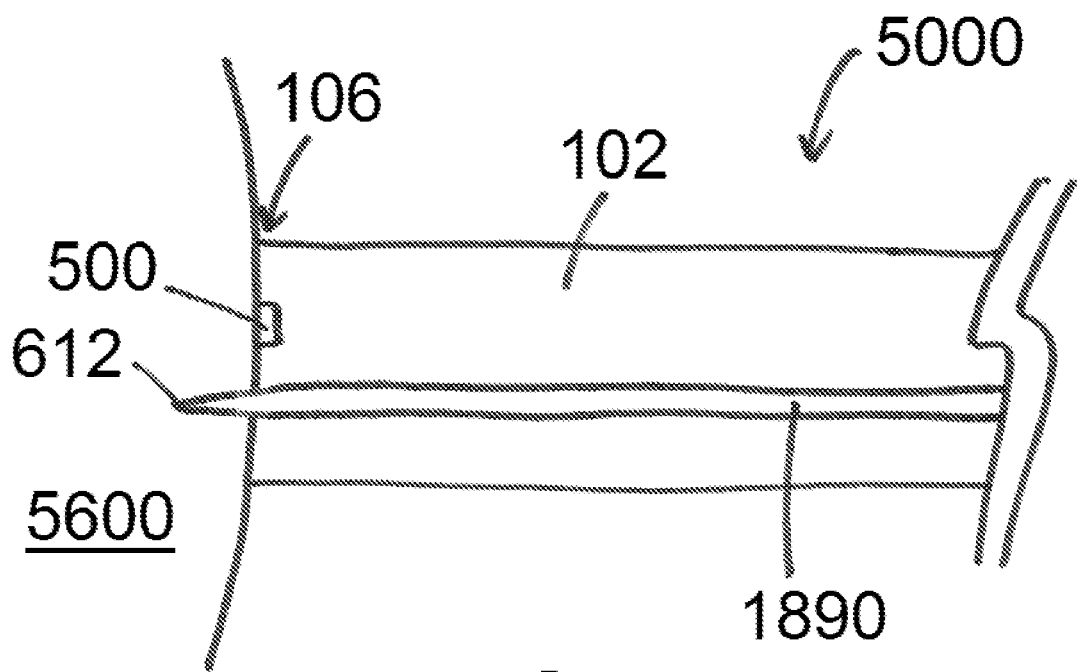
FIG. 28 shows a side view of a device having an electrode at a distal end, according to an exemplary embodiment of the present disclosure.
Figure 29:
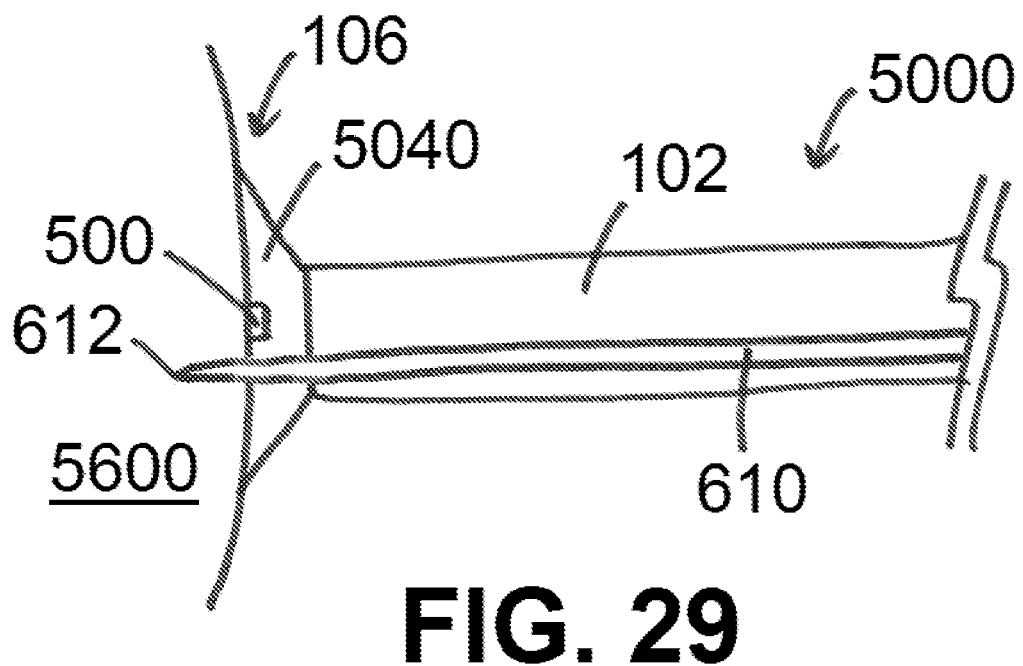
FIG. 29 shows a side view of a device having an electrode positioned upon a suction cup, according to an exemplary embodiment of the present disclosure.
Figure 34:
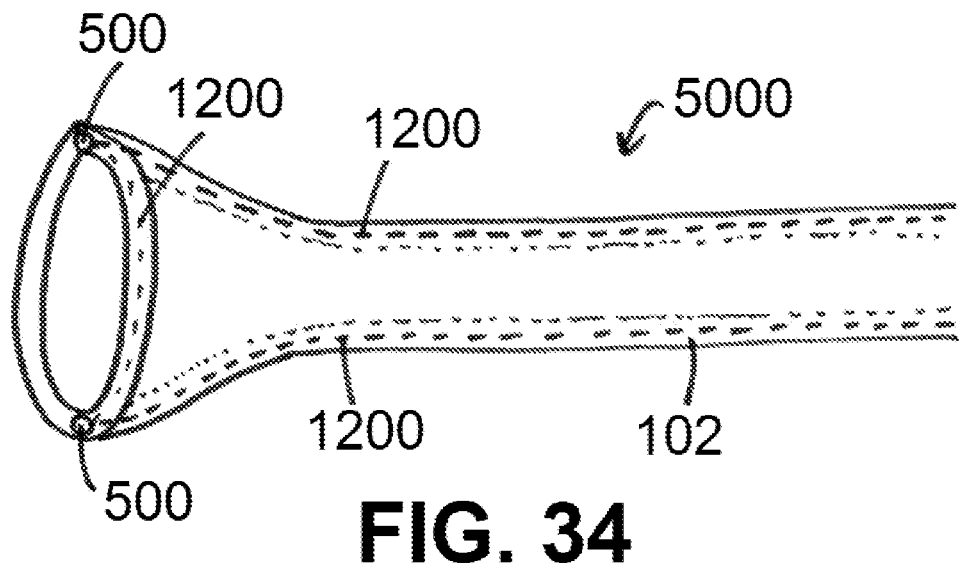
FIG. 34 shows a side perspective view of a device having at least one wire running therethrough, according to an exemplary embodiment of the present disclosure.
Figure 35:
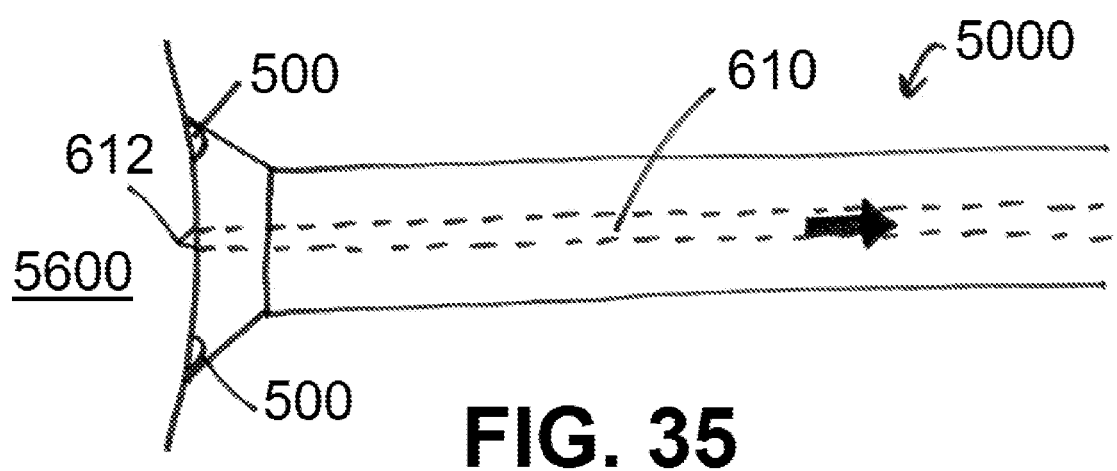
FIG. 35 shows a side view of a device suctionally engaged to a tissue with a needle contacting said tissue and completing a circuit sufficient to transmit data to a console coupled to said device via said needle, according to an exemplary embodiment of the present disclosure.

Additional device 5000 embodiments of the present disclosure are shown in FIGS. 28 and 29. As shown in FIG. 28, device 5000 comprises an electrode 500 present at a distal end 106 of device 5000, and as shown in FIG. 29, device 5000 comprises an electrode present at a suction cup 5040 at a distal end 106 of device 5000. In either embodiment, electrode 500 could obtain impedance/conductance data prior to or at the time of suction contact of device 5000 with tissue 5600. When a tip 612 of a needle 1890, such as positioned within device 5000 as shown in FIGS. 28 and 29, contacts and/or punctures tissue 5600, needle 1890 can act as a circuit ground, and impedance/conductance data obtained using electrode 500 would confirm suction contact and/or needle penetration. Such a circuit could be a simple circuit with current provided by electrode 500, a second electrode 500, etc., and grounded by needle 1890, or provided using a plurality of electrodes 500 at distal end 106 of device 5000 or along suction cup 5040. Needle 1890 or electrode(s) 500 on suction cup 5040, in various embodiments, can function/act as a circuit ground, with various combinations possible given the number of electrodes 500 used. This allows for various device 5000 configuration options (such as one, two, three, or more electrodes 500) to obtain bioimpedance data, the location(s) within the body the data is obtained from, as well as how the data is ultimately transmitted back, such as to console 240. In at least one embodiment, various wires 1200, such as shown in FIG. 34, are used to connect electrode(s) 500 to other parts of system 200, such as console 240, and/or to connect various electrode(s) 500 and other sensors 900, 910 to one another, in various embodiments. Wires 1200 can run through portions of suction cup 500 and/or through other portions of device 5000, such as through elongated body 5900 (the wall thereof) and/or within lumen 110. In at least one embodiment, data obtained using one or more of electrodes 500 and/or sensors 900, 910 could be transmitted to other parts of system 200, such as to console 240, via needle 1890 if needle 1890 is part of the overall circuit with electrode(s) 500 and/or sensor(s) 900, 910, such as in the direction of the arrow shown in FIG. 35.

Depending on the number and type(s) of electrodes 500 used, impedance/conductance data obtained by said electrodes could also be used to characterize the types of tissue, such as a fibrotic infarcted myocardium versus a healthy myocardium portion, as those different types/conditions of tissue would result in different impedance/conductance data. As devices 5000 referenced herein are flexible, control of needle 1890 penetration depth based upon a predetermined length of needle 1890 would be difficult. As such, impedance/conductance data obtained using electrode(s) 500 would identify needle tip 612 contact with the engaged tissue 5600, and then a penetration depth could be controlled from a proximal end 104 of device 5000, for example.

Figure 30:
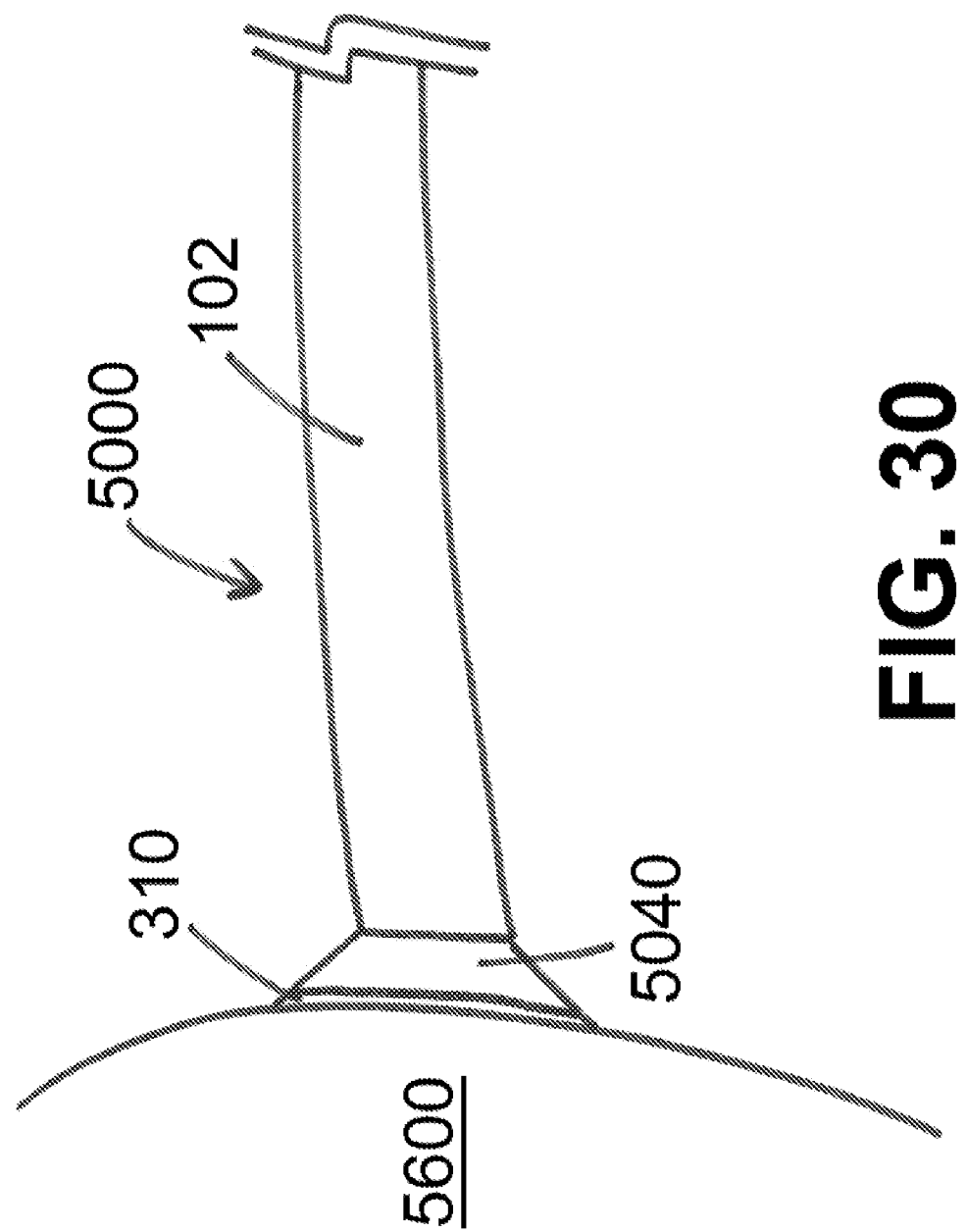
FIG. 30 shows a side view of a device suctionally engaging a tissue, according to an exemplary embodiment of the present disclosure.

An embodiment of a device 5000 of the present disclosure is shown in FIG. 30 suctionally engaged to a tissue 5600. As shown in FIG. 30, a first radiopaque element 310, configured as a conductive wire, circumscribes a tip of suction cup 5040 and is configured to measure bioimpedance of tissue 5600, such as a myocardium. The bioimpedance of myocardium would differ from that of blood, which is consistent with the disclosure above indicating that devices 5000 could obtain impedance/conductance data prior to and/or during tissue 5600 engagement, and that said data would differ depending on whether or not device 5000 engaged said tissue 5600. Aside from the ability to obtain bioimpedance data, the radiopacity of radiopaque element 310 would also be visualized under x-ray, for example, providing visual location data as well.

Furthermore, it is noted that the various portions of device 5000 embodiments having elements configured to obtain bioimpedance measurements, such as electrodes 500 and various radiopaque elements 310, 312 that may also be configured to obtain bioimpedance measurements, said portions may or may not contact tissue 5600 at various times when within a mammalian luminal organ or otherwise within the body. For example, and such as shown in FIGS. 25-27, radiopaque elements 310 and/or 312 may be configured to obtain impedance/conductance data (bioimpedance data) and also be detectable under x-ray, like a traditional impedance/conductance electrode 500. As such, the bioimpedance data can reflect when portions of device 5000 do not contact a luminal organ wall (an exemplary tissue 5600), such as when radiopaque elements 310, 312 do not contact said tissue 5600, and bioimpedance data can also reflect when portions of device 5000 do actually contact tissue 5600, whereby the bioimpedance data (such as, for example, cardiac conductivity) that would be several times less conductive than blood, for example. In at least one embodiment, bellow(s) 5800 can contact tissue 5600, and bioimpedance data obtained from radiopaque element 312 would reflect said tissue 5600 contact. Similarly, suction cup 5040 can contact tissue 5600, and bioimpedance data obtained from radiopaque element 310 would reflect said tissue 5600 contact.

Figure 31:
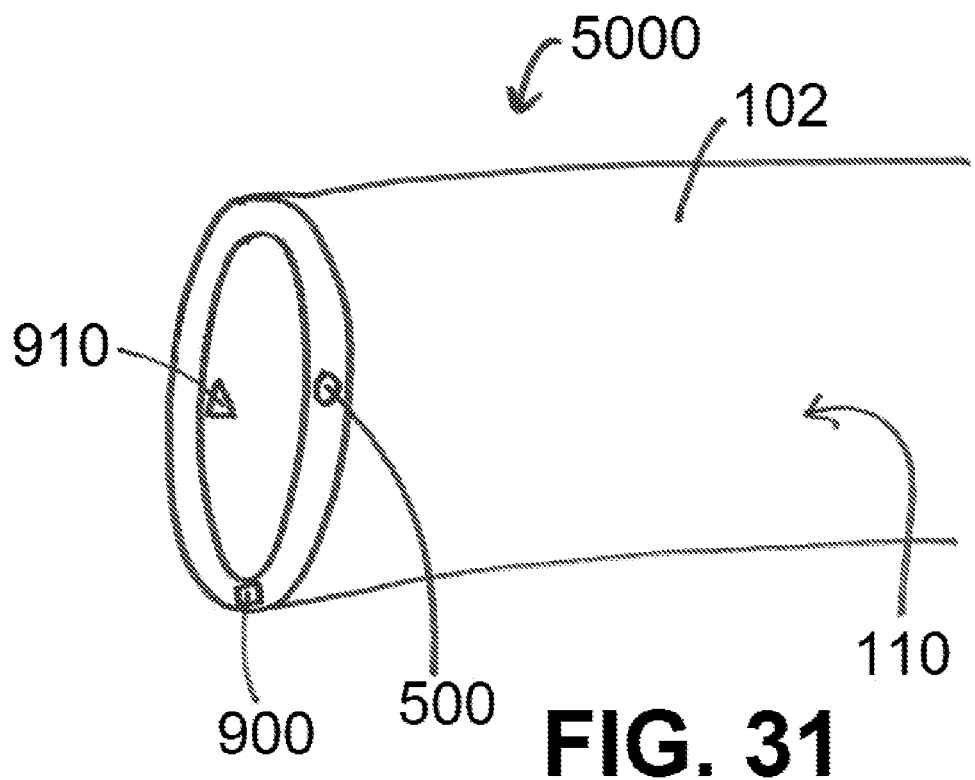
FIG. 31 shows a side perspective view of a device having an electrode, an optical element/sensor, and a pressure element/sensor, according to an exemplary embodiment of the present disclosure.
Figure 32:
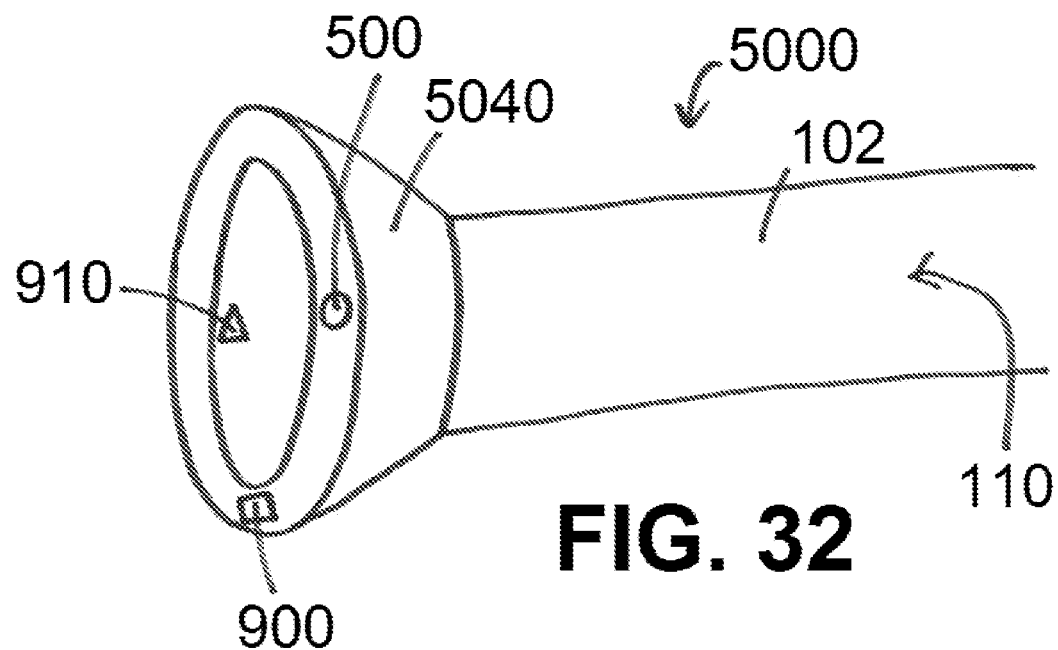
FIG. 32 shows a side perspective view of a device having a suction cup, an electrode, an optical element/sensor, and a pressure element/sensor, according to an exemplary embodiment of the present disclosure.

Additional device 5000 embodiments are shown in FIGS. 31 and 32. As shown therein, exemplary devices 5000 of the present disclosure may include one or more electrodes 500, one or more optical elements/sensors 900, and/or one or more pressure elements/sensors 910. Optical elements/sensors 900 may be positioned at a distal end 106 of device as coupled to elongated body 5900 (as shown in FIG. 31) or suction cup 5040 (as shown in FIG. 32). Pressure elements/sensors 910 may be positioned on a relative inside of device 5000, such as to be exposed at least partially to lumen 110, as shown in FIGS. 31 and 32, so to obtain pressure data from within lumen 110. Optical elements/sensors 900, such as lights, cameras, etc., can be operated to obtain optical data and transmit the same through device 5000 to console 240, for example, so to provide/use said data to a user to provide visual location information, such as to provide the user with confirmation that device 5000 has contacted a tissue 5600 of interest. Pressure elements/sensors 910, such as traditional pressure sensors or transducers, can be used in various embodiments to obtain pressure data within device 5000 and provide the same to the user, such as to indicate relatively higher pressure within device 5000 when device 5000 is suctionally attached to a tissue 5600 of interest. The existence of a threshold level of pressure within device 5000, for example, would indicate suctional engagement as may be desired.

Figure 33:
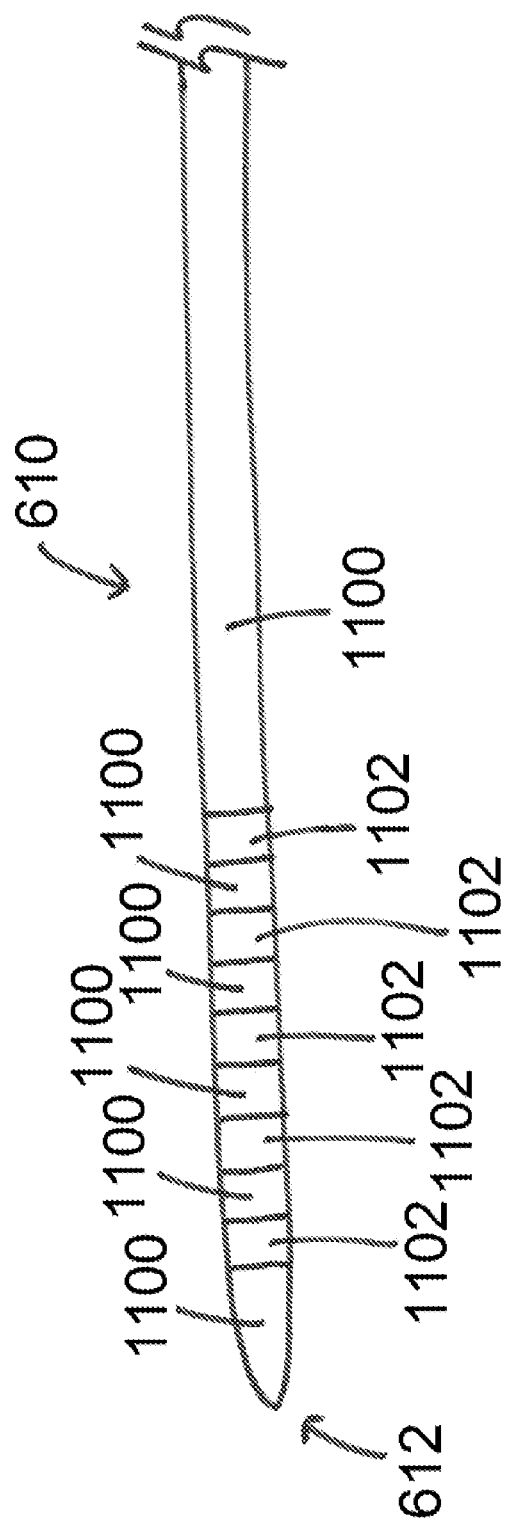
FIG. 33 shows a side view of a needle having conductive and non-conductive portions, according to an exemplary embodiment of the present disclosure.

An overall depth of needle 1890 penetration, such as when delivering a therapeutic substance, could be determined using a needle 1890 as shown in FIG. 33. As shown in FIG. 33, needle 1890 has a needle tip 612 with exposed conductive portions 1100 and covered portions 1102, which may alternate, as shown in FIG. 33, or have a different spatial configuration. As the various conductive portions 1100 and covered portions 1102 (also referred to as masked portions or non-conductive portions, such as those covered with a non-conductive material) would penetrate tissue 5600, changes in impedance/conductance could be identified using electrode(s) 500, for example, as the overall circuit at the surface of tissue 5600 would change depending on whether conductive portion 1100 or covered portion 1102 is then-present at a surface of tissue 5600. Identification and/or timing of various changes in impedance/conductance, in connection with advancement of needle 1890 into tissue 5600, would identify depth of needle tip 612 given the known lengths of said conductive portions 110 and/or covered portions.

As generally referenced above, the various devices 5000 and systems 200 of the present disclosure could be used so that a portion of device 5000 is introduced into a vasculature and advanced therethrough to a targeted tissue of interest. Using suction through a lumen 110 of device 5000, a distal end 106 of device 5000 (or a suction cup 5040 present at the distal end 106) can suctionally affix to a tissue, and other features of devices 5000 and/or systems 200 of the present disclosure could provide data, information, and/or feedback to a user to confirm suction engagement, such as a) operation of a vacuum gauge mechanism 150, such that a movable element 152 and/or an indication bar 154 moves as pressure increases, and/or b) by way of illumination and/or a color change of an indicator light 175 present at a proximal end 104 of device 5000, which would illuminate and/or change color based upon optical, impedance, and/or pressure data and/or changes of said data, and/or c) by way of identification of a radiopaque element 310, 312, and/or an electrode 500, present along device 5000, such as by under x-ray, and/or d) by way of movement of radiopaque elements 310, 312 toward each other, and/or e) by way of changes in impedance/conductance as detected using electrode(s) 500 alone or along with needle 1890, and/or f) as otherwise referenced above. Once suction engagement is confirmed, a needle 1890 (forming part of an exemplary system 200, in various embodiments) can be used to introduce a substance 230 via injection source 220 through needle 1890 and into tissue 5600 without fear of substance 230 getting to other areas of the body, as substance 230 that exits needle tip 612 that either does not enter tissue 5600 and/or that leaks from tissue 5600 would be suctionally removed through device 5000 under suction, preventing future embolization caused by migration of substance 230. Said process would allow for effective and safe treatment of a myocardial defect, such as by way of injection of a polymer, a stem cell, a drug (all exemplary substances 230) therein using needle 1890, for example.

The various devices 5000 and systems 200 referenced herein may include various other components, such as wires used to connect electrodes 5040, optical elements/sensors 900, pressure elements/sensors 910, and/or radiopaque elements 310, 312, for example, to other portions of devices 5000 and/or systems 200, such as to a console 240. The various devices 5000 and systems 200 referenced herein may also include various other devices and components used along with the same, such as sheaths, delivery catheters, and the like. Devices 5000 of the present disclosure may also be configured as engagement catheters 1810, depending on embodiments/features of said device 5000. In view of the same, the content and disclosure of U.S. Pat. No. 7,454,244 to Kassab et al. and U.S. Pat. No. 8,894,606 to Kassab et al. are incorporated herein in their entirety, as the various impedance and related aspects contained within U.S. Pat. No. 7,454,244 to Kassab et al. and the various catheter and engagement aspects contained within U.S. Pat. No. 8,894,606 to Kassab et al. could apply and/or be useful to generate and/or operate the various devices 5000 and/or systems 200 referenced herein.

While various embodiments of devices and systems for suction engagement and substance delivery and methods for using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A device, comprising:
an elongated body having a proximal end, a distal end, and at least one lumen extending from the proximal end to the distal end;
an engagement portion at the distal end of the elongated body, the engagement portion configured to engage a tissue adjacent thereto when the engagement portion contacts the tissue while suction is applied through the device;
at least one electrode present along the engagement portion and configured to contact the tissue when the engagement portion contacts the tissue and to obtain bioimpedance data from the tissue while suction is applied through the device;
a first radiopaque ring element disposed circumferentially around the engagement portion and configured to obtain bioimpedance data from the tissue when in contact with the tissue and while suction is applied through the device; and
a second radiopaque ring element disposed circumferentially around the engagement portion; wherein the first radiopaque ring element and the second radiopaque ring element are spaced apart from one another when no suction is applied through the device; and wherein the first radiopaque ring element and the second radiopaque ring element move toward one another when suction is applied through the device.

2. The device of claim 1, wherein the engagement portion comprises a compliant suction cup, and wherein the at least one electrode is present along the suction cup.

3. The device of claim 2, wherein the engagement portion further comprises a bellows adjacent to the suction cup, the bellows configured to move relative to the suction cup when suction is applied through the device.

4. The device of claim 1, wherein when a needle is positioned within the device and wherein when the needle and the at least one electrode contact the tissue while suction is applied through the device, a circuit is created between the at least one electrode and the needle, whereby the circuit is indicative of suction contact of the electrode to the tissue and/or needle contact of the tissue.

5. The device of claim 1, further comprising:
one or more optical sensors/electrodes present along the engagement portion and configured to obtain optical data and to transmit the optical data to a console coupled to the device.

6. The device of claim 1, further comprising:
one or more pressure elements/sensors present along a relative inside of the engagement portion and configured to obtain pressure data from within the at least one lumen of the device.

7. The device of claim 1, further comprising:
at least one wire extending from the proximal end of the device to the at least one electrode, the at least one wire configured to transmit data obtained from the at least one electrode through the at least one wire to a console coupled too the device.

8. The device of claim 1, further comprising:
a vacuum gauge mechanism positioned at a proximal end of the device, the vacuum gauge mechanism comprising a movable element configured to move relative to the device when suction is applied through the device.

9. The device of claim 8, wherein the movable element comprises an indication bar having indicia thereon.

10. A device, comprising:
an elongated body having a proximal end, a distal end, and at least one lumen extending from the proximal end to the distal end;
a compliant suction cup at the distal end of the elongated body, the suction cup configured to engage a tissue adjacent thereto when the suction cup contacts the tissue while suction is applied through the device;
a bellows adjacent to the suction cup, the bellows configured to move relative to the suction cup when suction is applied through the device;
a first radiopaque ring element disposed circumferentially around the suction cup and configured to obtain bioimpedance data from the tissue when in contact with the tissue and while suction is applied through the device; and
a second radiopaque ring element disposed circumferentially around the bellows; wherein the first radiopaque ring element and the second radiopaque ring element are spaced apart from one another when no suction is applied through the device; and wherein the first radiopaque ring element and the second radiopaque ring element move toward one another when suction is applied through the device.

11. The device of claim 10, further comprising:
at least one electrode present along the suction cup and configured to contact the tissue when the suction cup contacts the tissue and to obtain bioimpedance data from the tissue while suction is applied through the device.

12. A system, comprising:
a device, comprising:
an elongated body having a proximal end, a distal end, and at least one lumen extending from the proximal end to the distal end;
an engagement portion at the distal end of the elongated body, the engagement portion configured to engage a tissue adjacent thereto when the engagement portion contacts the tissue while suction is applied through the device;
at least one electrode present along the engagement portion and configured to contact the tissue when the engagement portion contacts the tissue and to obtain bioimpedance data from the tissue while suction is applied through the device;
a first radiopaque ring element disposed circumferentially around the engagement portion and configured to obtain bioimpedance data from the tissue when in contact with the tissue and while suction is applied through the device; and
a second radiopaque ring element disposed circumferentially around the engagement portion; wherein the first radiopaque ring element and the second radiopaque ring element are spaced apart from one another when no suction is applied through the device; and wherein the first radiopaque ring element and the second radiopaque ring element move toward one another when suction is applied through the device;
a needle configured for insertion within at least one lumen of the at least one lumens of the device; and
wherein when the at least one electrode and the needle contact the tissue, a circuit is created, whereby the circuit is indicative of suction contact of the electrode to the tissue and/or needle contact of the tissue.

13. The system of claim 12:
wherein the engagement portion comprises a compliant suction cup;
wherein the at least one electrode is present along the suction cup; and
wherein the engagement portion further comprises a bellows adjacent to the suction cup, the bellows configured to move relative to the suction cup when suction is applied through the device.

* * * * *